(12) United States Patent
Herweck et al.

(10) Patent No.: US 9,327,096 B2
(45) Date of Patent: May 3, 2016

(54) BODY LUMEN FLUID DELIVERY DEVICE

(75) Inventors: Steve A. Herweck, Wellesley, MA (US);
Ronit R. Furman, Watertown, MA (US)

(73) Assignee: Atrium Medical Corporation,
Merrimack, NH (US)

(*) Notice: Subject to any disclaimer, the term of this patent is extended or adjusted under 35 U.S.C. 154(b) by 1208 days.

(21) Appl. No.: 13/232,340

(22) Filed: Sep. 14, 2011

(65) Prior Publication Data

US 2012/0310085 A1    Dec. 6, 2012

Related U.S. Application Data

(60) Provisional application No. 61/492,439, filed on Jun. 2, 2011.

(51) Int. Cl.

| | | |
|---|---|---|
| *A61M 25/00* | (2006.01) | |
| *A61M 25/01* | (2006.01) | |
| *A61M 5/00* | (2006.01) | |
| *A61B 6/12* | (2006.01) | |
| *A61B 6/00* | (2006.01) | |
| *A61B 19/00* | (2006.01) | |

(52) U.S. Cl.
CPC ....... *A61M 25/0068* (2013.01); *A61M 25/0023* (2013.01); *A61B 6/12* (2013.01); *A61B 6/481* (2013.01); *A61B 2019/5466* (2013.01); *A61M 5/007* (2013.01); *A61M 25/005* (2013.01); *A61M 25/0108* (2013.01); *A61M 2025/0042* (2013.01); *A61M 2025/0046* (2013.01); *A61M 2025/0057* (2013.01); *A61M 2025/0073* (2013.01); *A61M 2025/0183* (2013.01)

(58) Field of Classification Search
CPC .......... A61M 25/005; A61M 25/0023; A61M 25/0108; A61M 25/007; A61M 2025/004; A61M 2025/0035; A61M 2025/0042; A61M 2025/0056; A61M 2025/0057; A61B 5/055; A61B 6/12; A61B 6/481; A61B 2019/5466
See application file for complete search history.

(56) References Cited

U.S. PATENT DOCUMENTS

| | | | | |
|---|---|---|---|---|
| 4,968,307 | A | * 11/1990 | Dake et al. ................... | 604/264 |
| 5,458,568 | A | 10/1995 | Racchini et al. | |
| 5,549,556 | A | * 8/1996 | Ndondo-Lay et al. ..... | 604/103.1 |
| 5,676,659 | A | * 10/1997 | McGurk ...................... | 604/527 |

(Continued)

FOREIGN PATENT DOCUMENTS

EP        2233165 A2    9/2010

OTHER PUBLICATIONS

International Search Report for International Patent Application No. PCT/US2011/51527, dated Jan. 25, 2012.

*Primary Examiner* — Andrew Gilbert

(57) ABSTRACT

A method and apparatus for fluid delivery enables navigation through tortuous, spatially restricted body anatomy to access narrow diameter body lumens for the continuous delivery of fluids, including therapeutic fluids, to the lumen in an atraumatic manner that avoids damage to the body lumen. The fluid delivery device can have a flexible conduit having a proximal end, a distal end, and a lumen extending along an interior of the flexible conduit providing a fluid flow path between the proximal and distal ends, where the lumen transitions into a micro-lumen exiting through a port through which a high concentration of fluid injected into the lumen exits laterally out along an image viewable zone at the distal end of the flexible conduit. The flexible conduit has a maximum outer diameter sized sufficient to navigate narrow diameter body lumens.

39 Claims, 10 Drawing Sheets

(56) References Cited

U.S. PATENT DOCUMENTS

| | | | |
|---|---|---|---|
| 5,743,051 A * | 4/1998 | Bergmann | 52/27 |
| 5,843,051 A * | 12/1998 | Adams | A61M 25/0102 604/164.01 |
| 6,231,570 B1 | 5/2001 | Tu et al. | |
| 6,602,241 B2 * | 8/2003 | Makower et al. | 604/509 |
| 6,604,054 B2 | 8/2003 | Lipscomb et al. | |
| 6,645,135 B1 * | 11/2003 | Bhat | 600/3 |
| 6,824,532 B2 | 11/2004 | Gills et al. | |
| 7,241,286 B2 * | 7/2007 | Atlas | A61B 1/00091 600/156 |
| 7,556,612 B2 * | 7/2009 | Voorhees | A61M 25/0097 604/264 |
| 8,292,841 B2 * | 10/2012 | Gregersen | A61M 1/3653 604/29 |
| 2004/0254525 A1 | 12/2004 | Uber et al. | |
| 2005/0090802 A1 | 4/2005 | Connors et al. | |
| 2006/0149350 A1 * | 7/2006 | Patel et al. | 623/1.11 |
| 2007/0202149 A1 | 8/2007 | Faucher et al. | |
| 2007/0280991 A1 * | 12/2007 | Glauser et al. | 424/426 |
| 2008/0058641 A1 * | 3/2008 | Shimko | 600/433 |
| 2008/0147040 A1 * | 6/2008 | Dikshteyn | 604/506 |
| 2009/0181937 A1 | 7/2009 | Faucher et al. | |
| 2009/0208552 A1 | 8/2009 | Faucher et al. | |
| 2010/0174183 A1 * | 7/2010 | Schwartz et al. | 600/433 |
| 2011/0264132 A1 * | 10/2011 | Strauss et al. | 606/194 |

* cited by examiner

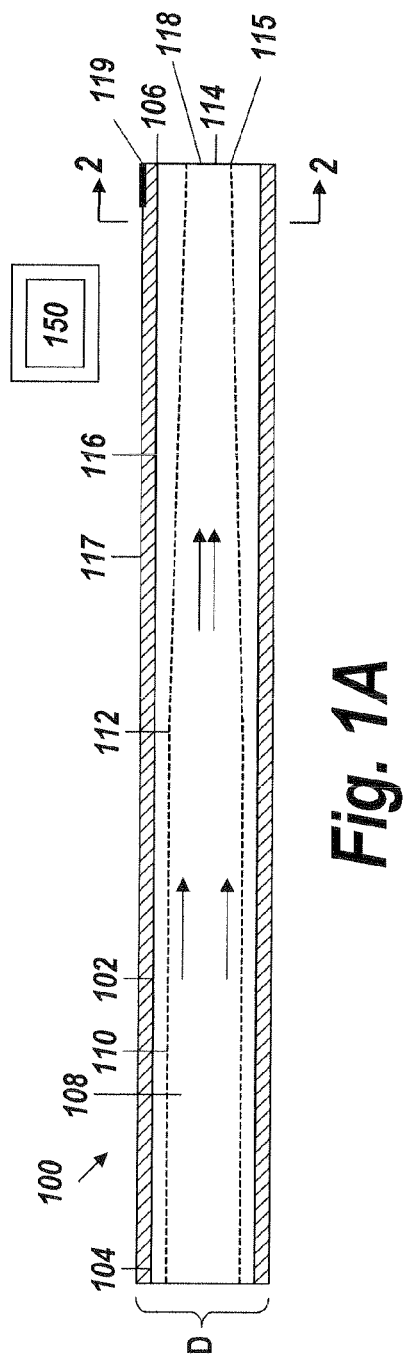
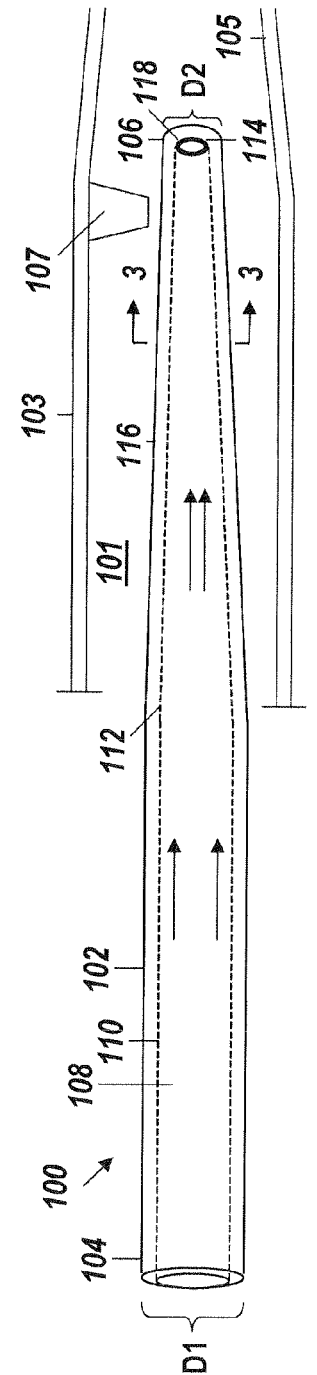
Fig. 1A
Fig. 1B

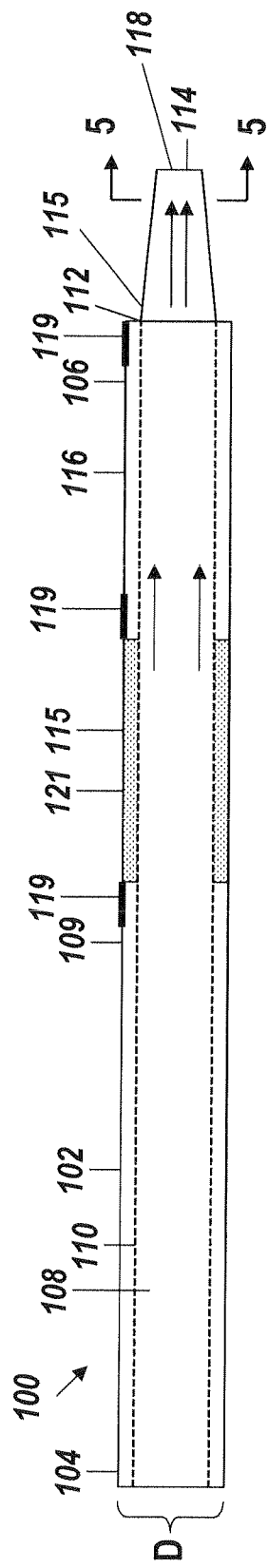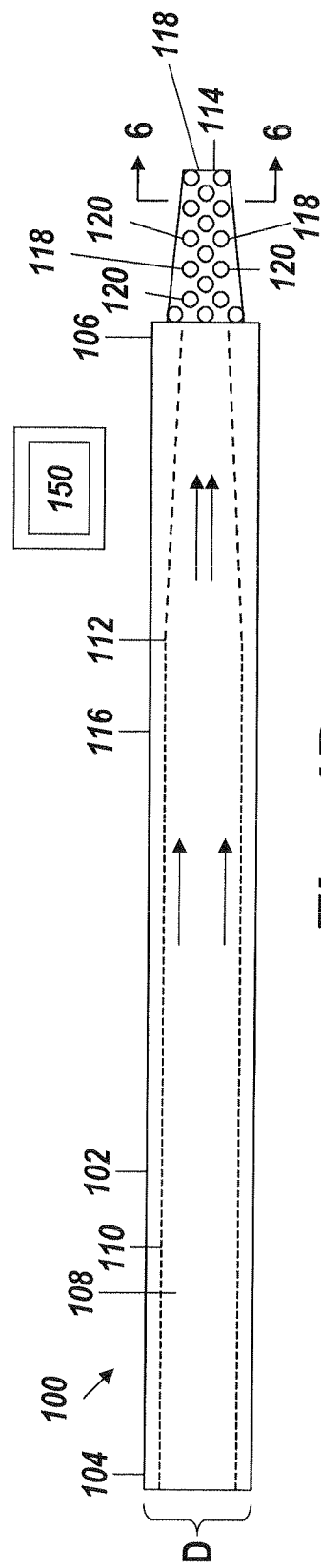

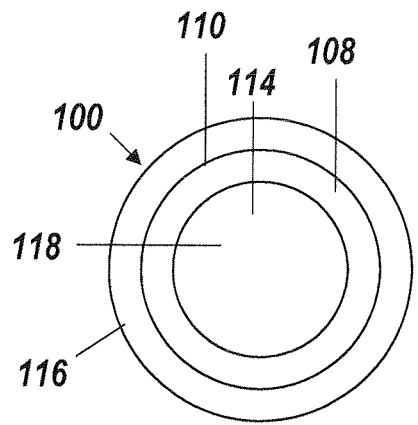 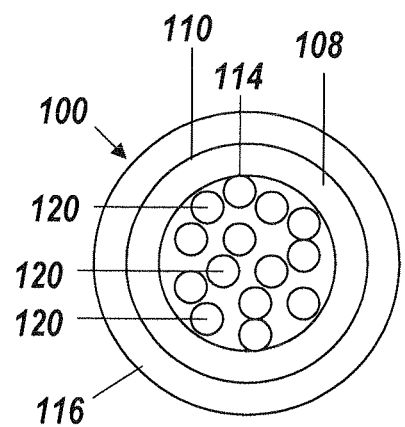
*Fig. 5A*  *Fig. 5B*
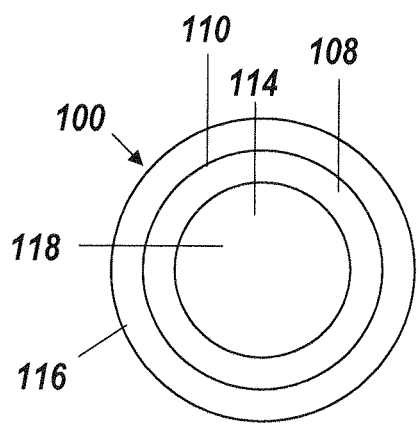 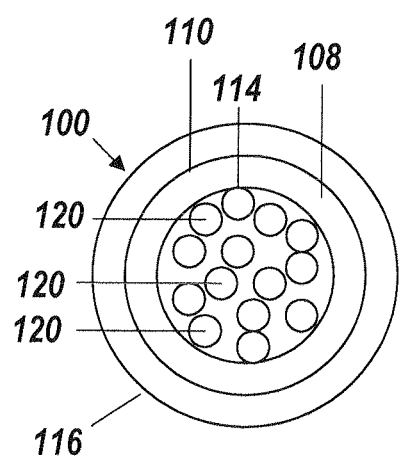
*Fig. 6A*  *Fig. 6B*

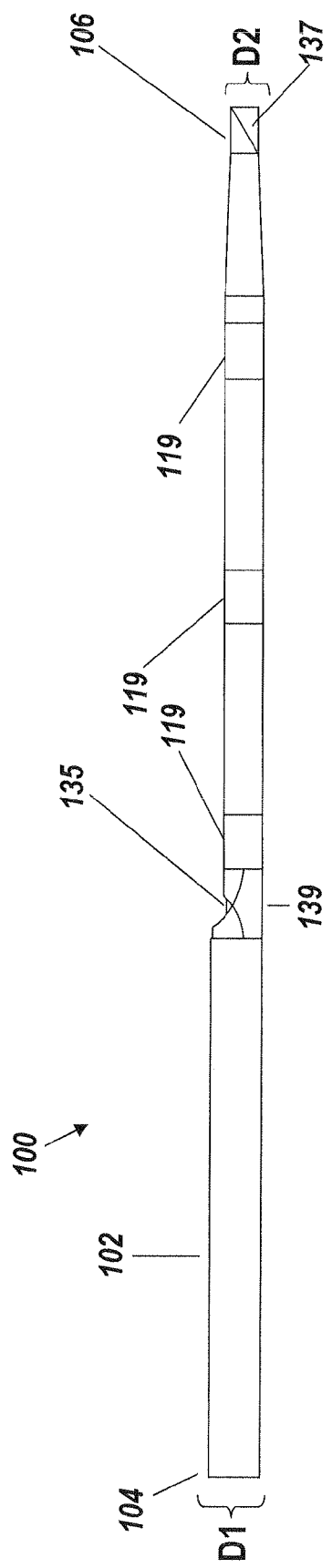

BODY LUMEN FLUID DELIVERY DEVICE

RELATED APPLICATION

This application claims priority to, and the benefit of, U.S. Provisional Application No. 61/492,439, filed Jun. 2, 2011, for all subject matter common to both applications. The disclosure of said provisional application is hereby incorporated herein by reference in its entirety.

FIELD OF THE INVENTION

The present invention relates to a fluid delivery device suitable for delivering a fluid to a treatment site within a patient's body, and more particularly to an image guided fluid delivery device for navigating tortuous, spatially restricted body anatomy to maintain a high concentration of a medication to a narrow diameter body lumen and within an image guided zone.

BACKGROUND OF THE INVENTION

In a wide range of medical treatment procedures, local therapeutic agent delivery through an open-ended delivery catheter, sheath or needle placed within a vein or artery of a body cavity is commonly used for systemic deliverable liquid and embolic agents. Hence, clinicians must pre-calculate the medication dose for its efficacy after dispersion following delivery within the body, as the medication quickly dilutes and diffuses to a significantly less concentration immediately after delivery with such open ended medical injectable devices placed within the body. Placement of one or more holes along the side wall of such delivery devices have been clinically shown to cause tissue damage under injection delivery pressures, creating a damaged area within the body. Such side wall hole delivery devices also do not provide for image viewable zones of delivery as they are indicated for systemic delivery of medication. Non-porous elastomeric and angioplasty balloon catheters have also been used to deliver therapeutic agents directly to treatment sites within a body cavity by creating systemic occlusion of the vessel or narrow lumen with the same undesirable clinical effects when the medication is uncontrollably delivered by syringe via jetting fluid out through the central lumen of such delivery device generally located on the distal end and side holes. Such devices provide no means to concentrate the medication without inducing either occlusion or trauma to the vessel, and without any image guidance means to determine where the concentration of medication is delivered. Therefore an atraumatic medication delivery device that provides a means to determine under image guidance the location of the highest concentration of medication delivered locally to a targeted treatment site, prior to systemic dilution and without vessel occlusion, may increase the efficacy and decrease the systemic loss of a prescribed medication bolus during injection, and reduce the need for larger volumes and concentrations of medication generally prescribed for systemic dilution during IV injection.

Micro porous balloon delivery devices have been demonstrated to enable a therapeutic agent to be delivered through small pores formed in the balloon portion itself creating a pressure limiting means by which to deliver a medication during inflation and vessel occlusion. A significant shortcoming common to such drug eluting porous conventional balloon catheters is that the multiple bonding zones required for attaching a porous delivery balloon to the catheter shaft, and its size, length and geometry of the balloon portion around the external shaft of the catheter limits the ability of the catheter to track around tortuous anatomy, significantly restricting access to various hard to reach and remote body cavity treatment sites for localized delivery of therapeutic agents. For example, both conventional porous and non-porous balloon catheters may encounter difficulty accessing smaller vessel treatment sites having narrow, or partially occluded or diseased lumens leading up to the treatment site. In addition, the sites at which conventional balloon catheters are able to be positioned for treatment are limited by the size and geometry of the folded balloon material and bonding sites on the outside of the catheter shaft. Further, in those situations in which a balloon catheter is able to access more difficult to reach sites, or smaller sites, the expansion of the medication delivery balloon itself to release the therapeutic agent may not be able to be positioned to maximize drug concentration at the treatment site without causing damage to the narrowed channel or vessel. In some instances, the damage may be caused by a jetting action of the fluid emitting from the balloon or delivery device and impacting the tissue. In these situations, conventional balloon catheters therefore may not be suitable for localized delivery of therapeutic agents to many narrow, partially occluded and remote treatment sites within the body.

SUMMARY

There is a need for a fluid delivery device that navigates tortuous, spatially restricted body anatomy to access narrow diameter body lumens and partially occluded lumens for the continuous delivery of fluid medication, maintaining the highest concentration of a delivered medication at the targeted treatment site within an image guided and image viewable zone, and which avoids jetting and pressure damage to the localized treatment area. The present invention is directed toward further solutions to address this need, in addition to having other desirable characteristics.

In accordance with example embodiments of the present invention, a fluid delivery device includes a flexible conduit having a proximal end and a distal end. An image viewable zone can be disposed along an exterior of the flexible conduit at a predetermined location suitable for delivery of a fluid from the device. The image viewable zone can be defined by one or more markers viewable in vivo by an imaging device. A lumen can extend along an interior of the flexible conduit providing a fluid flow path between the proximal end and the distal end for a fluid injected into the conduit, the lumen transitioning into a micro-lumen exiting from the flexible conduit at a port at the image viewable zone. The port can be configured in such a way as to direct a relatively high concentration of fluid primarily laterally along the image viewable zone. The micro-lumen can have a maximum cross-sectional flow area of 0.01 mm. The flexible conduit can have a maximum outer diameter of 1.1 mm or less.

In accordance with aspects of the present invention, the fluid delivery device can further include a plurality of micro-lumens transitioning to ports, each port enabling the fluid to exit at the image viewable zone primarily laterally and maintain a high concentration of fluid along a length of the image viewable zone, wherein each of the micro-lumens have a maximum cross-sectional flow area of 0.01 mm. Fluid flowing through the fluid flow path can exit the plurality of micro-lumens transitioning to ports into a target body lumen at a rate insufficient to damage tissue within the target body lumen.

In accordance with aspects of the present invention, the device can be constructed of one or more biocompatible materials. The one or more biocompatible materials can be a thermoplastic polymer. The thermoplastic polymer can include PEBA, nylon HDPE, PTFE, FEP, ETFE, ePTFE and combinations thereof.

In accordance with aspects of the present invention, the device can further include a reinforcement incorporated into the flexible conduit imparting flexibility and kink resistance to the flexible conduit. The reinforcement can include a braided wire structure, slotted metal tube, or a helical coil structure. The reinforcement can be constructed of a material selected from the group consisting of stainless steel, cobalt, chromium, platinum, nitinol, and/or combinations thereof.

In accordance with aspects of the present invention, the flexible conduit can have an outer diameter that varies along the image viewable zone imparting improved flexibility and torque response to the flexible conduit during navigation in vivo. The flexible conduit can include multiple sections, each section constructed of materials of varying durometer, imparting improved flexibility and torque response during navigation in vivo. The flexible conduit can have varying durometer ranges along its length ranging from about 50 to about 100 shore A and from about 40 to about 80 shore D.

In accordance with aspects of the present invention, the one or more markers can be heavy radiopaque metal component materials. The heavy radiopaque metal component materials can include PtIr, Au, tungsten, and/or combinations thereof. The one or more markers can include radiopaque fillers incorporated into one or more locations along the flexible conduit. The radiopaque fillers can include barium sulfate, tungsten, and/or bismuth subcarbonate. The one or more markers can take the form of a coating applied, painted, printed, etched, grafted, or laminated onto the flexible conduit forming the image viewable zone.

In accordance with embodiments of the present invention, fluid flowing through the fluid flow path exits the port into a target body location at a rate insufficient to damage tissue. In further accordance with aspects of the present invention, if a fluid having a viscosity of 1 cps at 25° C. is supplied to the flexible conduit at a pressure of between about 1 atmosphere and about 4 atmospheres, a flowrate through the flexible conduit does not exceed 17 cc/min. If a fluid having a viscosity of 5 cps at 25° C. is supplied to the flexible conduit at a pressure of between about 1 atmosphere and about 4 atmospheres, a flowrate through the flexible conduit does not exceed 4 cc/min. If a fluid having a viscosity of 11 cps at 25° C. is supplied to the flexible conduit at a pressure of between about 1 atmosphere and about 4 atmospheres, a flowrate through the flexible conduit does not exceed 2 cc/min.

In accordance with embodiments of the present invention, the device can further include a rapid exchange port proximal to the port at the image viewable zone, wherein the relative distances between the rapid exchange port, the port at the image viewable zone, and the one or more markers, provide a variable image guidance means through which navigation of the flexible conduit through tortuous, spatially restricted body channels can be optimized.

In accordance with aspects of the present invention, the flexible conduit can have a hydrophilic exterior surface. The flexible conduit can have a hydrophobic exterior surface. The device can further include a coating disposed on an exterior surface of the flexible conduit. The coating can be a lubricious coating. The coating can be a therapeutic coating. The therapeutic coating can include omega-3 fatty acids. The fluid can be a medication, a therapeutic agent, a diagnostic agent, or any combination thereof. The fluid can be an emulsion, a nanoemulsion, or a cellular suspension comprised of cellular, genetic or viral material. The fluid can be at least one of antioxidants, anti-hypertensive agents, anti-inflammatory agents, anti-infective agents, antibiotic agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for gene delivery, agents for local tissue perfusion, nitric oxide donating derivatives, thrombus-inducing agents, vasodilators, neuroprotective agents, neuronal healing agents, saline, and/or contrast media. The fluid can include abciximab. The fluid can include eptifibatide. The fluid can include TPA. The fluid include at least one of a contrast agent or a dye.

In accordance with aspects of the present invention, the fluid delivery device can be a medical treatment device for treating a body lumen or cavity. The fluid delivery device can be a medical diagnostic device for diagnosing a disease in a body lumen or cavity. The imaging device can utilize image viewing technology in the form of one or more of radiography, magnetic resonance imaging, nuclear imaging, photo acoustic imaging, thermal imaging, or ultrasound.

In accordance with aspects of the present invention, the image viewable zone can permit a user of the fluid delivery device to observe the injected fluid being delivered in real-time such that the user can determine the maximum concentration of fluid to deliver to a target treatment site within a target body location.

In accordance with example embodiments of the present invention, a method for delivery of a fluid to a target body location includes providing a flexible conduit, wherein the flexible conduit includes a proximal end, a distal end, an image viewable zone disposed along an exterior of the flexible conduit at a predetermined location suitable for delivery of a fluid from the device, the image viewable zone defined by one or more markers viewable in vivo by an imaging device. The conduit further includes a lumen extending along an interior of the flexible conduit providing a fluid flow path between the proximal end and the distal end for a fluid injected into the conduit, the lumen transitioning into a micro-lumen exiting from the flexible conduit at a port at the image viewable zone, the port configured in such a way as to direct a relatively high concentration of fluid primarily laterally along the image viewable zone. The micro-lumen can have a maximum cross-sectional flow area of 0.01 mm, and the flexible conduit can have a maximum outer diameter of 1.1 mm or less. The method can include advancing a guidewire to a target body location to be treated with a therapeutic fluid. The flexible conduit can be advanced along the guidewire under image guidance utilizing the imaging device to view the image viewable zone until the distal end of the flexible conduit reaches a lumen within the target body location. The fluid can be supplied into the flexible conduit causing the fluid to exit through and out the port at the image viewable zone at a rate insufficient to damage tissue proximal to the device. The imaging device can utilize image viewing technology in the form of one or more of radiography, magnetic resonance imaging, nuclear imaging, photo acoustic imaging, thermal imaging, or ultrasound.

In accordance with embodiments of the present invention, a method for localized gene delivery, can include providing a flexible conduit, wherein the flexible conduit comprises, a proximal end and a distal end, an image viewable zone disposed along an exterior of the flexible conduit at a predetermined location suitable for delivery of a fluid from the device, the image viewable zone defined by one or more markers viewable in vivo by an imaging device, and a lumen extending along an interior the flexible conduit providing a fluid flow path between the proximal end and the distal end for a fluid injected into the conduit. The lumen can transition into a micro-lumen exiting from the flexible conduit at a port at the image viewable zone. The port can be configured in such a way as to direct a relatively high concentration of fluid primarily laterally along the image viewable zone, wherein the micro-lumen has a maximum cross-sectional flow area of 0.01 mm, and wherein the flexible conduit has a maximum outer diameter of 1.1 mm or less. The method can further include advancing a guidewire to a target body location to be treated with a gene therapy vector. The flexible conduit can be advanced along the guidewire under image guidance utilizing the imaging device to view the image viewable zone until the distal end of the flexible conduit reaches a lumen within the target body location. The fluid containing a first gene therapy vector can be supplied into the flexible conduit at a first time point, causing the fluid to exit through and out the port at the image viewable zone for the localized delivery of the first gene therapy vector within the target body location at a rate insufficient to damage tissue proximal to the flexible conduit.

In accordance with aspects of the present invention, the supplied fluid can contain multiple gene therapy vectors. The gene therapy vector can contain multiple transgenes. The step of supplying the fluid containing the gene therapy vector can be performed at multiple different time points over a period of time. The method can further include optionally preflushing the flexible conduit with a serum albumin solution.

In accordance with aspects of the present invention, the method can further include supplying the fluid containing a second gene therapy vector into the flexible conduit at a second time point, causing the fluid to exit through and out the port at the image viewable zone for the localized delivery of the second gene therapy vector within the target body location at a rate insufficient to damage tissue proximal to the flexible conduit.

In accordance with aspects of the present invention, the method can further include supplying the fluid containing an $n^{th}$ gene therapy vector into the flexible conduit at an $n^{th}$ time point, where n is an integer greater than two, causing the fluid to exit through and out the port at the image viewable zone for the localized delivery of the $n^{th}$ gene therapy vector within the target body location at a rate insufficient to damage tissue proximal to the flexible conduit. Some of the $n^{th}$ gene therapy vectors can contain the same transgene and some of the $n^{th}$ gene therapy vectors can contain a different transgene.

In accordance with aspects of the present invention, the imaging device can utilize image viewing technology in the form of one or more of radiography, magnetic resonance imaging, nuclear imaging, photo acoustic imaging, thermal imaging, or ultrasound.

BRIEF DESCRIPTION OF THE FIGURES

These and other characteristics of the present invention will be more fully understood by reference to the following detailed description in conjunction with the attached drawings, in which:

FIG. 1A is a side elevational view in cross-section of a fluid delivery device according to one aspect of the present invention, Illustrating a monolithic construction of the device having a uniform diameter as the lumen transitions into a micro-lumen at the distal end;

FIG. 1B is a side elevational view in cross-section of a fluid delivery device according to one aspect of the present invention, illustrating a monolithic construction of the device having a non-uniform diameter as the lumen transitions into a micro-lumen at the distal end;

FIG. 4A is a side elevational view in cross-section of a fluid delivery device according to one aspect of the present invention, illustrating a stereolithic construction of the device having a flexible conduit and a cap within which the lumen begins to transition into a micro-lumen at the distal end;

FIG. 4B is a side elevational view in cross-section of a fluid delivery device according to one aspect of the present invention, illustrating a stereolithic construction of the device having a flexible conduit and a cap in which the lumen begins to transition into a micro-lumen inside distal end of the flexible conduit;

FIG. 5A is a transverse cross-section view of the fluid delivery shown in FIG. 4A according to one aspect of the present invention, taken along line 5-5, illustrating the micro-lumen at the distal end of the cap;

FIG. 5B is a transverse cross-section view of the fluid delivery shown in FIG. 4A according to one aspect of the present invention, taken along line 5-5, illustrating a plurality of micro-lumens at the distal end of the cap;

FIG. 6A is a transverse cross-section view of the fluid delivery shown in FIG. 4B according to one aspect of the present invention, taken along line 6-6, illustrating the micro-lumen at the distal end of the cap;

FIG. 6B is a transverse cross-section view of the fluid delivery shown in FIG. 4B according to one aspect of the present invention, taken along line 6-6, illustrating a plurality of micro-lumens at the distal end of the cap;

FIG. 10B is a side elevational view in cross-section of a fluid delivery device according to one aspect of the present invention, illustrating the relative dimensions and distances between the port and markers which provide a means for variable image guidance.

DETAILED DESCRIPTION

Figure 2A:
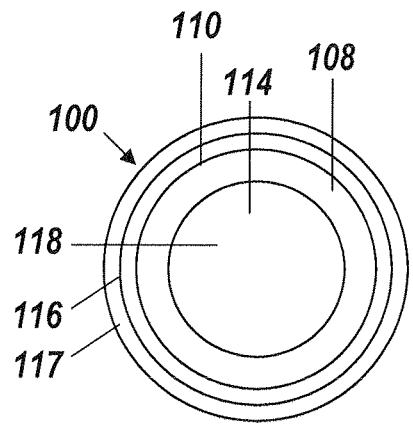
FIG. 2A is a transverse cross-section view of the fluid delivery shown in FIG. 1A according to one aspect of the present invention, taken along line 2-2, illustrating the micro-lumen at the distal end.
Figure 2B:
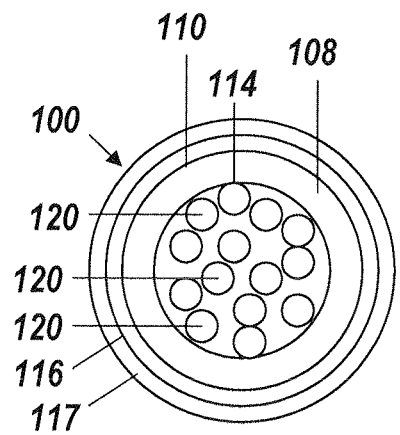
FIG. 2B is a transverse cross-section view of the fluid delivery shown in FIG. 1A according to one aspect of the present invention, taken along line 2-2, illustrating a plurality of micro-lumens at the distal end.
Figure 3A:
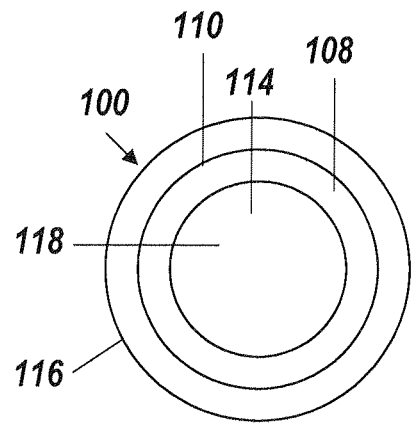
FIG. 3A is a transverse cross-section view of the fluid delivery shown in FIG. 1B according to one aspect of the present invention, taken along line 3-3, illustrating the micro-lumen at the distal end.
Figure 3B:
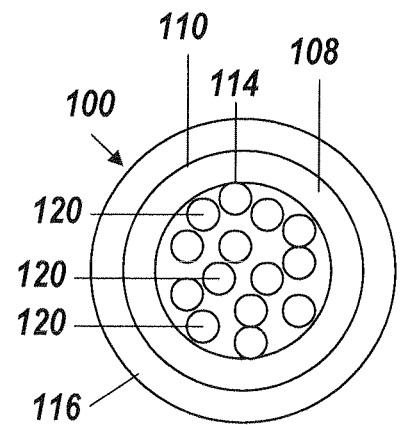
FIG. 3B is a transverse cross-section view of the fluid delivery shown in FIG. 1B according to one aspect of the present invention, taken along line 3-3, illustrating a plurality of micro-lumens at the distal end.

An illustrative embodiment of the present invention relates to use of a fluid delivery device structured to navigate tortuous, spatially restricted body anatomy having narrow body channel diameters (e.g., as narrow as about 1 mm or less) for the high concentration delivery of a fluid, such as a medication, therapeutic agent, or diagnostic, to a target treatment area within the body. The present invention makes use of a biocompatible, flexible conduit having a maximum outer diameter sized in such a way as to enable navigation of narrow body channels (e.g., vessels), and a micro-lumen terminating within an image viewable zone along the flexible conduit provided with a pre-determined cross-sectional flow area for continuous localized delivery of high concentrations of the fluid to fill the entire treatment area within the narrow body channel around the outside of the image viewable zone along the flexible conduit at a pressure sufficient to minimize and or avoid damage to surrounding tissue (e.g., equal to about arterial pressure). Said differently, the delivery device is sufficiently flexible and constructed to navigate to difficult to reach, and/or narrowly configured, locations via image guidance directed by a catheter guidewire that has been positioned within the targeted treatment area of the body for atraumatic injection of the maximum concentration of a fluid to a targeted tissue location within the body along the image viewable medication delivery zone.

FIGS. 1A through 10C, wherein like parts are designated by like reference numerals throughout, illustrate example embodiments of a fluid delivery device according to the present invention. Although the present invention will be described with reference to the example embodiments illustrated in the figures, it should be understood that many alternative forms can embody the present invention. One of skill in the art will additionally appreciate different ways to alter the parameters of the embodiments disclosed, such as the size, shape, or type of elements or materials, in a manner still in keeping with the spirit and scope of the present invention.

A fluid delivery device 100 having a flexible conduit 102 designed to navigate tortuous, spatially restricted body anatomy (e.g., cavities, vessels, arteries, etc.) defined by narrow lumen diameters for the continuous high concentration delivery of a medication through a port and primarily laterally along an image viewable zone, placed within the target treatment area within the body is illustrated in FIGS. 1A, 1B, 4A, 4B, 7, 9, 10A, 10B and 10C. Generally, the flexible conduit 102 of the fluid delivery device 100 has a proximal end 104, a distal end 106, and a lumen 108 extending along an interior 110 of the flexible conduit. The lumen 108 provides a fluid flow path (represented by horizontal arrows) between the proximal end 104 and the distal end 106 through which a fluid flowing through the lumen can flow at a controlled rate out through an image viewable location 115 or image viewable zone 144 for a prescribed length determined by one or more markers 119 that are detectable via imaging, such as image detectable radiopaque markers, for example. The image viewable location 115 or image viewable zone 144 provided by the one or more markers 119 permit a user of the fluid delivery device 100 to observe in real-time the concentration of a fluid being delivered, in vivo. In accordance with some example embodiments, the one or more markers 119 permit the user to determine the fluid concentration being delivered in real-time so that the user can deliver the highest possible concentration of fluid medication to a targeted treatment site in the body.

At a predetermined distance between the proximal end 104 and the distal end 106 of the flexible conduit 102, the lumen 108 transitions at a transition point or region 112 from the lumen 108 into a micro-lumen 114 to enable flow of fluid along the fluid flow path out and around the external surface of the positioned delivery portion of the device within the body. Although the transition point or region 112 illustrated in FIG. 1A is located at about halfway between the proximal end 104 and the distal end 106, the transition point or region 112 can begin at other predetermined distances between the proximal end 104 and distal end 106 of the flexible conduit 102, depending on the particular application. This way, the transition point or region 112 can be located more proximally or more distally with respect to the micro-lumen 114 to further increase the concentration of medication around the outside of the portion placed within the treatment area of the body, as understood by one of skill in the art. The transition at the transition point or region 112 provides the flexible conduit 102 with a first maximum cross-sectional flow area before the transition point or region 112 and at least a second maximum cross-sectional flow area after the transition point or region 112. Providing a first maximum cross-sectional flow area and at least a second maximum cross-sectional flow area helps to control the back pressure of the medication flow rate out through the medication lumen of the flexible conduit.

The second maximum cross-sectional flow area after the transition point or region 112 is defined by the lumen geometry between the transition point or region 117 and the distal end 106 of the flexible conduit 102. Such lumen geometry is illustrated in FIGS. 1A and 113 as having a funnel shape, although other suitable geometries can be used to vary the maximum cross-sectional flow areas at the distal end of the flexible conduit, as understood by one of skill in the art. Although FIG. 1A shows the second maximum cross-sectional flow area after the transition point or region 112 as decreasing in a progressive manner, it should be appreciated that the second maximum cross-sectional flow area after the transition point or region 112 may increase along at least a portion of the lumen as long as maximum cross-sectional flow area at the micro-lumen is decreased relative to the first maximum cross-sectional flow area.

The flexible conduit 102, optionally can include a guidewire lumen (not shown) extending along at least a portion of the exterior surface 116 of the flexible conduit 102 for rapid exchange of the flexible conduit during use.

The flexible conduit 102 can be coupled to a fluid source (not shown) to selectively produce a fluid, such as water, a contrast medium, or saline, or a therapeutic agent, for example, to the lumen 108 of the flexible conduit 102 to flow along the fluid flow path and exit at an image guided location 115 through the micro-lumen 114 for delivery of the fluid medication to a body lumen. The fluid source can be used to control the flowrate of the fluid flowing along the fluid flow path through the conduit 102. In accordance with one example embodiment, if a fluid having a viscosity of 1 cps at 25° C. is supplied to the flexible conduit 102 at a pressure of between about 1 atmosphere and about 4 atmospheres, the flowrate through the conduit does not exceed 17 cc/min. In accordance with another example embodiment, if a fluid having a viscosity of 5 cps at 25° C. is supplied to the flexible conduit 102 at a pressure of between about 1 atmosphere and about 4 atmospheres, the flowrate through the conduit does not exceed 4 cc/min. In accordance with yet another example embodiment, if a fluid having a viscosity of 11 cps at 25° C.

is supplied to the flexible conduit 102 at a pressure of between about 1 atmosphere and about 4 atmospheres, the flowrate through the conduit does not exceed 2 cc/min. Other fluid flowrates can be maintained depending on the particular application by modifying the fluid viscosity and pressure, as understood by one of skill in the art.

Figure 9:
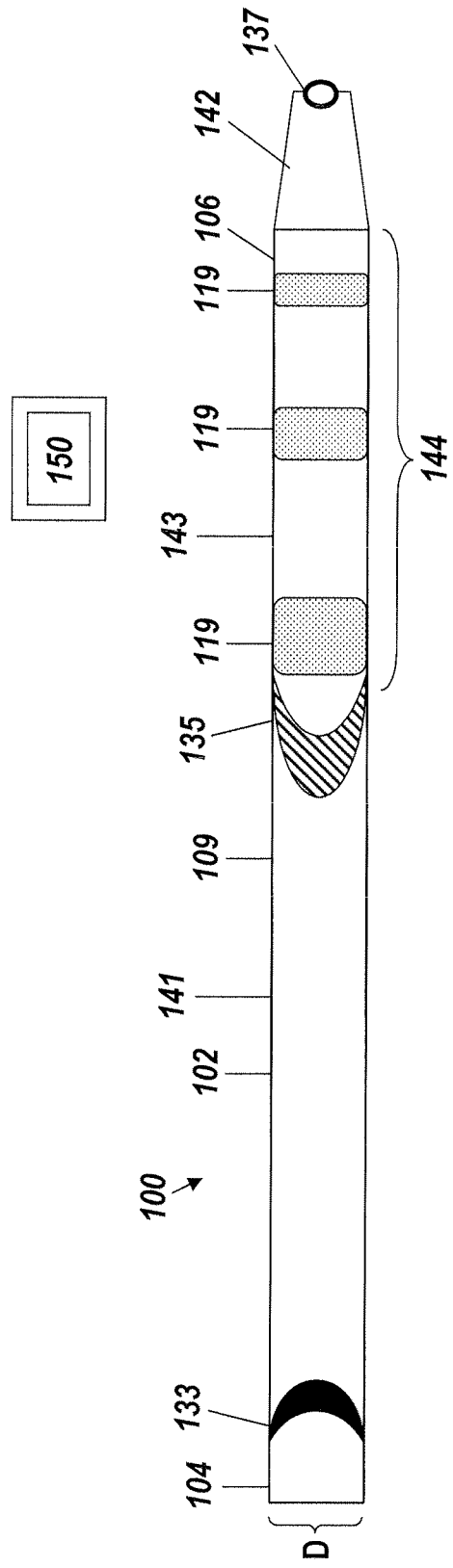
FIG. 9 is a top view of a fluid delivery device according to one aspect of the present invention.

The flexible conduit 102, optionally can include port 135 for infusing fluid (as shown in FIG. 9 and FIG. 10). The fluid infusion port 135 allows for fluid delivery to a targeted treatment site within a body lumen at a pressure sufficient to minimize or avoid damage to the body lumen (e.g., without jetting). The fluid infusion port 135 achieves such fluid delivery through its shape, which comprises an elongated half-funnel with side wall baffles (shown in FIG. 10). The shape of the fluid infusion port 135 also provides for a low fluid exit angle, which is parallel to the central longitudinal axis of the flexible conduit 102, causing the fluid to exit primarily laterally along the conduit 102 length rather than perpendicular or outward from the conduit 102. In addition to preventing jetting of fluid, the low fluid exit angle of the fluid infusion port 135 permits the flexible conduit to deliver fluid to a target body lumen in a way that fills the entire space between the body lumen and the flexible conduit 102 proximate to the one or more markers 119 disposed on the flexible conduit. Said differently, the fluid infusion port 135 delivers fluid primarily laterally along an image viewable zone 144 around the outside of the flexible conduit 102 to a narrow body channel without jetting fluid into the walls of the narrow body channel, so as to avoid or minimize damage to the narrow body channel. The image viewable zone 144 permits a user of the fluid delivery device 100 to observe and determine the concentration of fluid being delivered in real time so that the user can deliver and maintain the highest possible concentration of a fluid medication to a target treatment site within a body along the outside of the image viewable zone 144 of the flexible conduit 102. This way, the fluid delivery device 100 of the present invention is capable of effectively delivering a maximum possible concentration of a therapeutic agent to a localized region of the body. In other words, the fluid delivery device 100 makes possible the delivery of the maximum and most effective concentration of a therapeutic agent using direct image guidance utilizing an imaging device 150 to view the image viewable zone 144 during use. In certain embodiments, the flexible conduit can be provided with multiple ports 135 (e.g., fluid infusion ports) along the length of the flexible conduit. In some embodiments, each of the fluid infusion ports 135 may be provided with a fluid lumen. In some embodiments, each of the fluid infusion ports 135 may use the same fluid lumen. In some embodiments, some fluid infusion ports 135 may be provided with a distinct fluid lumen while some fluid infusion ports may share the same fluid lumen.

The flexible conduit 102 is constructed from a biocompatible material. In accordance with some example embodiments, the biocompatible material is a thermoplastic polymer. Examples of suitable thermoplastic polymers include, but are not limited to polyether block amides (PEBA), polyurethanes, engineering thermoplastics, such as Hytrel (Du Pont), PTFE or FEP, ETFE. In certain embodiments, the biocompatible material may include a reinforcement to increase flexibility and kink resistance of the flexible conduit while maintaining a low profile and thin-walled flexible conduit. Placement of the reinforcement in the wall of the flexible conduit can be done in accordance with known methodologies and structures, as would be readily appreciated by one of skill in the art. Examples of suitable reinforcements include braided wire structures, slotted metal tube, or helical coil structures. In such embodiments, the reinforcement can be constructed of any combination of stainless steel, cobalt, chromium, platinum, or nitinol materials.

The flexible conduit 102 is preferably generally tubular in shape, although other cross-sections, such as rectangular, oval, elliptical, or polygonal, can be utilized, depending on a particular application. The cross-section of the flexible conduit 102 may be continuous and uniform along the length of the flexible conduit 102 between the proximal end 104 and distal end 106, such as the example embodiment illustrated in FIG. 1A. However, in alternative embodiments, the cross-section can vary in size and/or shape along the length of the flexible conduit 102, as illustrated in FIG. 1B. In certain embodiments, the flexible conduit 102 may be designed to have a variable stiffness or flexibility along its length using transitions in cross section, shape and/or size of the flexible conduit and/or wall thickness. In certain embodiments, the materials used to construct the flexible conduit 102 may vary and transition along the length of the flexible conduit to impart stiffness transitions. In instances in which a reinforcement is used, the reinforcement may vary along the length of the flexible conduit 102 to impart desired flexibility characteristics and/or transitions to the flexible conduit. As understood by one of skill in the art, these characteristics can be modified to optimize the level of delivery performance in narrow and tortuous body channels.

Referring again now to FIG. 1A, the flexible conduit 102 is provided with a maximum outer diameter D sized in such a way as to enable navigation through the tortuous, spatially restricted anatomy of a body lumen to be treated. The combination of a maximum outer diameter D and a flexible construction permits the conduit 102 to navigate tortuous, spatially restricted anatomy, under image guidance over a guidewire, leading to a target body lumen for the localized delivery of large volumes of a fluid having maximum concentrations of a medication to the target body lumen. The maximum outer diameter D of the flexible conduit 102 can be designed to navigate body lumens defined by narrow lumen diameters, such as vessels of the neurovasculature, distal coronary vessels, or peripheral vessels, to name a few examples. In accordance with some example embodiments, the maximum outer diameter D of the flexible conduit 102 permits the flexible conduit to reach more distal locations proximate to an organ targeted body location for treatment, e.g., organ, tissue space, body channel, etc. In accordance with some example embodiments, the maximum outer diameter D of the flexible conduit 102 permits the fluid delivery device 100 of the present invention to access minute capillary channels for localized delivery of the highest concentration of a medication fluid along an image viewable zone 144 of the flexible conduit 102 to treat the minute capillary channels, e.g., deliver an effective amount of therapeutic agent. It is worth noting that by providing localized access to such minute capillary channels, the present fluid delivery device 100 is able to deliver locally an effective amount of the therapeutic agent at high concentrations in such a way that not only is difficult via conventional means (e.g., systemic or intravenous) but also that avoids causing systemic side effects. The present fluid delivery device 100 can be sized and dimensioned to pass through a range of lumen sizes that are generally slightly larger than the device itself. As understood by those skilled in the art, the range of lumen sizes through which the present fluid delivery device 100 can be sized and dimensioned to pass through may depend on the actual channel size, channel tortuousity, and the nature and extent of channel obstructions. Of course, the fluid delivery device can pass through a range of lumen sizes that are much larger than the device itself. In one example, a fluid delivery device 100 of the present invention is provided with a flexible conduit 102 having a maximum outer diameter D of about 1.1 millimeter. The maximum outer diameter D of the flexible conduit 102, however, can be customized depending on the application according to the manufacturing methods of the present invention.

In alternative embodiments, such as the example illustrated in FIG. 1B, the flexible conduit 102 can be provided with a maximum outer diameter D1 and a minimum outer diameter D2. Providing the flexible conduit 102 with a minimum outer diameter D2 at the distal end 106 permits the present fluid delivery device 100 to access more difficult to reach locations within a body channel 101 for the atraumatic delivery of fluid to the body channel. A cross section of such body channels 101 is illustrated in FIG. 1B. As shown in FIG. 1B, such difficult to reach body channels 101 may have a larger diameter proximal portion 103 and a more narrow diameter distal portion 105. In accordance with one example embodiment, the minimum outer diameter D2 at the distal end 106 permits the fluid delivery device 100 to access distal portions of a body channel lumen 101 into which the maximum outer diameter D1 is unable to access due to size and geometrical limitations. In accordance with another example embodiment, the minimum outer diameter D2 at the distal end 106 permits the fluid delivery device 100 to navigate beyond partially occluded portions 107 of a body lumen 101. In accordance with some example embodiments, the more difficult to reach locations in which the present fluid delivery device 100 is able to access include body cavities, channels, or lumens in areas adjacent to capillary channels. The maximum outer diameter of the flexible conduit 102 enables the fluid delivery device 100 to be positioned adjacent to capillary channels for treatments in which delivering high concentrations of a medication fluid under image guidance without systemic dilution would be useful. For example, the fluid delivery device 100 can be used for image guided chemotherapy in oncology applications for maximizing the highest concentration of a chemotherapeutic agent along an image viewable zone 144 of the flexible conduit 102 directly and locally to the minute capillary channels supporting a tumor. This way, systemic side effects traditionally associated with larger drug doses of chemotherapeutic agents common to conventional non-image guidance IV means can be avoided and the chemotherapeutic agent can be delivered effectively to the tumor in optimal concentrations as determined by the user as the medicated fluid is being delivered under image guidance in the image viewable zone 144 along the outside of the flexible conduit 102 to the minute capillary channels in real-time. In accordance with some example embodiments, the present fluid delivery device 100 can be used for high localized concentration of fluid medications to remote and difficult to reach organ cavities. In accordance with some example embodiments, the present fluid delivery device can be used to achieve high localized concentrations of fluid medications to target treatment sites adjacent to an organ sourced by connecting capillary channels. For example, the fluid delivery device 100 can be deployed within the vessels adjacent to such organs, e.g., the prostate, gall bladder, pancreas, or brain, for example, where high concentrations of fluid medication can impart a more efficacious therapeutic effect to the organ than larger conventional systemic medication doses. In instances where the organs adjacent to such vessels are comprised of tumors or cancerous tissue, the present fluid delivery device 100 can be used to deliver fluid medication to the vessels adjacent to the capillary sourced tumor in the highest possible drug concentration. Examples of such capillary sourced tumors which the present fluid delivery device 100 can reach for image guided delivery of optimal concentrations of a fluid medication along an image viewable zone 144 on the outside of the flexible conduit 102 for treatment of the capillary sourced tumors include, but are not limited to, tumors associated with a vessel, organ or organ cavity, a joint capsule, a ligament sheath, a nerve sheath, e.g., spinal cord, etc.

As shown in FIG. 1B, the maximum outer diameter D1 is substantially uniform along at least a portion of the flexible conduit 102 from the proximal end 104 to the transition point or region 112. The maximum outer diameter D1 is substantially non-uniform along at least a portion of the flexible conduit 102 from the transition point or region 112 to the distal end 106. As noted above, the predetermined distance at which the transition point or region 112 is located longitudinally on the flexible conduit 102 can be tailored to suit the needs of a particular application. This way, the portion of the flexible conduit 102 having a substantially non-uniform maximum outer diameter D1 can be increased or decreased to adjust the access profile of the flexible conduit 102. As understood by a person of skill in the art, increasing the longitudinal length of the portion of the flexible conduit 102 having the substantially non-uniform diameter maximum outer diameter D1 increases the access profile of the distal end 106 of the flexible conduit 102 terminating with a minimum outer diameter D2.

Looking again at FIG. 1A, the flexible conduit 102 has an exterior surface 116 onto which a coating 117 can be disposed. Although the coating 117 is only shown in the embodiment illustrated in FIG. 1A, it should be appreciated that the coating can be similarly implemented in the embodiments illustrated in the other figures in which the coating is not shown. As used herein, the term "coating" refers to a material that forms a layer or film on or around a substrate (e.g., a micro-lumen fluid delivery device). In accordance with certain exemplary embodiments, the coatings may be formed by depositing a coating material on the substrate in a substantially continuous manner such that the entire substrate is coated. As used herein, the phrase "coating material" refers to any materials that may be applied or deposited onto, over or around a substrate to form a coating. Alternatively, in accordance with certain exemplary embodiments the coatings may be formed or otherwise deposited on the substrate in a partial or interrupted manner, such that the substrate is not entirely coated with the coating material (e.g., depositing the coating material on the exterior of an image guided micro-lumen fluid delivery device, such that a coating is not formed on the interior of such device). In accordance with certain exemplary embodiments (e.g., when the coating is applied to a flexible substrate) the coating 117 is also flexible. Coatings can be applied or deposited to substrates in any, desired thickness.

In accordance with certain exemplary embodiments, the coating material or coating 117 comprises one or more triglycerides, glycerides and/or fatty acids (e.g., omega-3 fatty acids such as EPA, DHA and ALA). In accordance with certain exemplary embodiments, the coating material or coating 117 is formed from or comprises an oil composition (e.g., fish oil). In accordance with certain exemplary embodiments, the coating material or coating comprises an oil composition, wherein the oil composition comprises one or more triglycerides, glycerides and/or fatty acids, as taught for example, in US Publication No. 20070202149, US Publication No. 20090181937, and US Publication No 20090208552, the teachings of which are incorporated by reference herein in their entirety. In accordance with certain exemplary embodiments, the coating material is formed from one or more triglycerides, glycerides and/or fatty acids cross-linked to each other in a substantially random or non-polymeric configuration.

The coating 117 can be a hydrophilic or hydrophobic coating dependant on the particular treatment applications. For example, fluid delivery devices 100 constructed of ePTFE, a naturally hydrophobic material, can be coated with a hydrophilic coating to provide the fluid delivery device with a hydrophilic exterior surface 116. A suitable hydrophilic coating is formed using PHOTOLINK® chemistry available from Surmodics of Eden Prairie, Minn. The coating 117 can be a lubricious coating to provide the fluid delivery device 100 with improved maneuverability as the image guided flexible conduit 102 navigates the tortuous, spatially restricted body anatomy. The coating 117 can also be a therapeutic coating which imparts a therapeutic benefit, such as an anti-inflammatory effect, to tissue proximal to the flexible conduit 102 within a target body lumen. Of course, the therapeutic coating can also confer such a therapeutic effect as the flexible conduit 102 navigates the tortuous, spatially restricted body anatomy leading up to the target body lumen.

In instances in which the coating is a therapeutic coating, the coating 117 can be formed of a number of different agents and compositions. For example, the coating can be a non-polymeric, biologically compatible coating. As used herein to describe the coatings of the present invention, the phrase "non-polymeric" refers to a macromolecular structure comprising multiple monomeric units which are not bound to each other in a regular or repeating pattern or configuration (i.e., such monomeric units are bound or cross-linked to each other in a substantially random configuration). For example, in accordance with some example embodiments, the coatings described herein are formed by or comprise one or more of triglycerides, glycerides and fatty acids, wherein such triglycerides, glycerides and fatty acids are all bound or cross-linked to each other in a substantially random and non-repeating configuration. Cross-linking of the triglycerides, glycerides and/or fatty acids may be catalyzed by curing such triglycerides, glycerides and/or fatty acids, or alternatively by curing an oil composition comprising such triglycerides, glycerides and/or fatty acids. Curing with respect to the present invention generally refers to thickening, hardening, or drying of a material brought about by heat, UV, or chemical means. In accordance with certain example embodiments, the intermolecular bonds which cross-link, for example, triglycerides, glycerides and fatty acids, comprise one or more of the following bonds: hydrogen bonds, ester bonds, ether bonds, lactone bonds, carbon-carbon bonds, ionic bonds, van der Waals forces, etc. In accordance with certain example embodiments, the intermolecular bonds which cross-link, for example, the triglycerides, glycerides and fatty acids in an oil composition to form the coating 117, are easily hydrolysable (e.g., lactone bonds, delta lactone bonds). The coating 117 can be formed entirely of a single substance, or can be formed using a mixture, aggregate, compilation, composition, and the like, of two or more substances, including one or more different therapeutic agent nano-particles, one or more of which can be a therapeutic agent having therapeutic properties, and/or biological effects to the targeted tissue location. As used herein, the phrase "therapeutic drug and/or agent", "therapeutic coating", "medication" and variations thereof, are utilized interchangeably herein to indicate single drug or multiple therapeutic drugs, single or multiple therapeutic agents, or any combination of single or multiple drugs, agents, or bioactive substances. Such drugs or agents include, but are not limited to, those listed in Table 1 herein. As such, any subtle variations of the above phrase should not be interpreted to indicate a different meaning, or to refer to a different combination of drugs or agents. The present invention is directed toward improved delivery of therapeutic drugs and/or agents, or any combination thereof, as understood by one of skill in the art.

In accordance with one example embodiment, the coating 117 can be formed of a non-polymeric, biologically compatible, oil or fat, such as a non-polymeric bio-absorbable cross-linked gel derived at least in part from a fatty acid. In accordance with certain example embodiments, the coating 117 is bioabsorbable. As used herein the term "bioabsorbable" refers to the ability of a substance (e.g., a coating) to be consumed by, penetrate or otherwise be absorbed by cells or tissues. In accordance with certain example embodiments, the bioabsorbable substance (e.g., a non-polymeric cross-linked gel coating) must be hydrolyzed (e.g., enzymatically or by other biological processes), metabolized or otherwise reduced into its constituent parts (e.g., fatty acids and/or glycerides) to be bioabsorbable by cells or tissues. In accordance with certain example embodiments, the bioabsorbable substance, whether considered as a whole or its constituent parts, does not cause an inflammatory response when bioabsorbed by cells or tissues.

There are a number of different therapeutic agents that are either lipophilic, or do not have a substantial aversion to oils or fats. Such therapeutic agents can be mixed with the oil or fat, without forming a chemical bond, and delivered to a targeted tissue location within a patient in accordance with the teachings of the present invention. The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, prodrugs, and any additional desired therapeutic agents such as those listed in Table 1 herein.

Turning now to FIG. 4A, the flexible conduit 102, optionally can have one or more markers 119 that are detectable utilizing an imaging device 150 incorporated into the flexible conduit 102 at any location between the proximal end 104 and distal end 106 of the flexible conduit 102 to provide an image-guided location 115, or image viewable zone 144. for visualization of the particular location of the flexible conduit 102 during use, in vivo. In accordance with an example embodiment, the flexible conduit 102 has one or more radiopaque markers 119 incorporated into the flexible conduit 102 at any location between the proximal end 104 and the distal end 106 of the flexible conduit 102 to provide an image-guided location 115, or image viewable zone 144, for visualization of the particular location on the flexible conduit 102 during use, in vivo. In accordance with some example embodiments, the flexible conduit 102, optionally can have a plurality of radiopaque markers 119 incorporated into the flexible conduit at any position between the proximal end 104 and the distal end 106 to provide multiple image guided locations 115 on the flexible conduit 102. As illustrated in the example embodiment illustrated in FIG. 4A, the flexible conduit 102 can be provided with three radiopaque markers 119 incorporated at different positions between a medial portion 109 and the distal end 106 of the flexible conduit to form an image viewable zone 144. It should be appreciated, however, that the number of radiopaque markers 119 employed may vary depending on the application, as understood by one of skill in the art. For example, up to 2, 3, 4, 5 or more radiopaque markers may be incorporated into the flexible conduit.

Although the radiopaque marker 119 is only shown in the embodiment illustrated in FIG. 4A, it should be appreciated that the radiopaque marker can be similarly implemented in the embodiments illustrated in the other figures in which the radiopaque marker is not shown. Suitable radiopaque markers are readily available from commercial sources and can be adapted for use with the fluid delivery device 100 of the present invention according to conventional methods, as understood by one of skill in the art.

Still looking at FIG. 4A, the flexible conduit 102, optionally can have a sleeve 121 covering at least a portion of the flexible conduit 102. As illustrated in the example embodiment in FIG. 4A the sleeve 121 covers a portion of the flexible conduit 102 between the medial portion 109 and the distal end 106 of the flexible conduit. However, the extent to which the sleeve 121 covers the flexible conduit 102 may vary depending on the application, as understood by one of skill in the art. Although the sleeve 121 is only shown in the embodiment illustrated in FIG. 4A, it should be appreciated that the sleeve can be similarly implemented in the embodiments illustrated in the other figures in which the sleeve is not shown. In accordance with certain example embodiments, the sleeve 121 provides improved slip performance and trackability through tortuous, spatially restricted body anatomy to improve deliverability of the fluid delivery device to a target treatment site within a body lumen. In accordance with certain example embodiments, the sleeve 121 is a protective sleeve. In accordance with certain example embodiments, the sleeve 121 is a polymer sleeve, such as a fluoropolymer e.g., ePTFE, for example. Although any suitable polymer can be used to form the sleeve 121. In accordance with certain example embodiments, the sleeve 121 may be filled with one or more radiopaque markers 119 (not shown).

Referring back now to the lumen 108 in the example embodiment illustrated FIG. 1A. As noted above, and as shown in FIG. 1A, the lumen 108 transitions into a micro-lumen 114 which forms an exit 118 through and out an image guided location 115, or image viewable zone 144, at the distal end 106 of the flexible conduit 102. As the lumen 108 begins to transition to the micro-lumen 114 at the transition point or region 112 between the proximal end 104 and distal end 106 of the flexible conduit 102, the cross-sectional flow area of the lumen 108 begins to decrease in a gradual manner. The gradually decreasing cross-sectional flow area continually restricts fluid flow to the micro-lumen 114 along the fluid flow path of the flexible conduit 102 and helps to control the back pressure of the medication flow rate out through the medication lumen of the flexible conduit 102. The gradually decreasing cross-sectional flow area approaching the distal end 106 of the flexible conduit 102 provides the micro-lumen 114 with an optimized maximum cross-sectional flow area. The optimal maximum cross-sectional flow area of the micro-lumen 114 can be tailored to meet the needs of a particular application, as understood by one of skill in the art, to alter the rate of fluid exiting the flexible conduit 102 through the micro-lumen 114. The combination of the gradually decreasing cross-sectional flow area and the maximum cross-sectional flow area of the micro-lumen 114 permits fluid flowing through the fluid flow path to exit through the micro-lumen 114 at an image guided location 115, or image viewable zone 144, into a target body lumen in a weeping fashion, such that damage to tissue proximal to the distal end 106 of the flexible conduit 102 within the target vessel is avoided. Damage to tissue proximal to the distal end 106 of the flexible conduit 102 is minimized or avoided due, in part, to the ability of micro-lumen 114 to deliver fluid medication about the image guided location 115, or image viewable zone 144, of the flexible conduit 102 at minimal pressure (e.g., arterial pressure) such that high concentrations of medication are maintained at the targeted treatment area within an image viewable zone. It should be noted that the residence time of the medication delivered to a target treatment site within a body lumen at the image guided zone exceeds the residence time needed for the fluid delivery device to deliver a medication dose sufficient to maintain therapeutically effective concentrations at the target treatment site for extended durations of time.

FIGS. 1A and 1B illustrate exemplary embodiments showing a monolithic construction of the fluid delivery device 100 of the present invention in which the flexible conduit 102 and the micro-lumen 114 form a singular, unitary article of generally homogeneous material, in accordance with one embodiment of the present invention. As illustrated in FIGS. 1A and 1B, the micro-lumen 114 is disposed at an image guided location 115 adjacent to the distal end 106 of the flexible conduit 102, and entirely inside the flexible conduit such that the distal end of the micro-lumen terminates approximately parallel to the distal end of the flexible conduit. In such instances, the exit 118 of the flexible conduit 102 forms a one-dimensional exit through which fluid flowing through the flexible conduit can be delivered under image guidance to a target body lumen. The one-dimensional exit is substantially perpendicular to the plane defined by the longitudinal axis of the flexible conduit 102. The one-dimensional exit concentrates the flow of fluid in a single direction into a target body lumen for delivery of fluid into the lumen.

In accordance with other exemplary embodiment, FIGS. 4A and 4B illustrate a stereolithic construction of the fluid delivery device 100 in which the flexible conduit 102 and the micro-lumen 114 form plural, distinct articles. It should be noted that in such instances, the flexible conduit 102 and the micro-lumen 114 can be formed of a generally heterogeneous material. Alternatively, the flexible conduit 102 and the micro-lumen 114 can be formed of generally homogeneous material. It should also be noted that stereolithic construction of the fluid delivery device 100 operates in a substantially similar manner to the fluid delivery device 100 having a monolithic construction as described above. In accordance with the example embodiment illustrated in FIG. 4A, the transition point or region 112 at which the lumen 108 of the flexible conduit 102 transitions into the micro-lumen 114 begins at the distal end 106 of the flexible conduit. However, the transition point or region 112 can begin at any predetermined distance between the proximal end 104 and the distal end 106 of the flexible conduit, such as shown in the example embodiment illustrated in FIG. 4B. By providing a micro-lumen 114 that extends from, and is distinct from, the flexible conduit 102, the micro-lumen can be provided with a greater number of micro-lumens 120. In contrast to the micro-lumen 114 situated entirely inside the distal end 106 of the flexible conduit 102 (FIGS. 1A and 1B) which provides only a one-dimensional exit through which fluid flowing through the flexible conduit can be delivered to a target body channel, the micro-lumen 114 illustrated in FIGS. 4A and 4B provides a multi-dimensional exit through which fluid can be delivered to the target body channel. FIG. 4B shows an example embodiment of such a micro-lumen 114 having a plurality of micro-lumens 120 forming a multi-dimensional fluid exit. In such instances, a plurality of exits 118 form the multi-dimensional fluid exit 118. The multi-dimensional fluid exits are substantially perpendicular to the plane defined by the longitudinal axis of the flexible conduit 102 as shown in FIG. 6B, as well as substantially parallel to the same plane as shown in FIG. 4B. In accordance with some example embodiments, the multi-dimensional fluid exit 118 directs fluid into a target body channel lumen in a direction parallel to the longitudinal axis of the flexible conduit 102 while simultaneously directing fluid into the target body channel in a direction transverse to the longitudinal axis of the flexible conduit. In accordance with some example embodiments, the multi-dimensional fluid exit 118 directs fluid into a target body channel vessel radially in about 360 degrees of directionality about the micro-lumen 114. Directing fluid into a target vessel radially in about 360 degrees of directionality about the micro-lumen 114 provides for a continuous volume of fluid to be delivered circumferentially about the distal end 106 of the flexible conduit 102 to a target body channel. Delivering a continuous volume of fluid circumferentially about the distal end 106 of the flexible conduit 102 in this manner permits the fluid delivery device to direct fluid simultaneously directly towards the channel wall and into the channel lumen with an atraumatic force.

Figure 7:
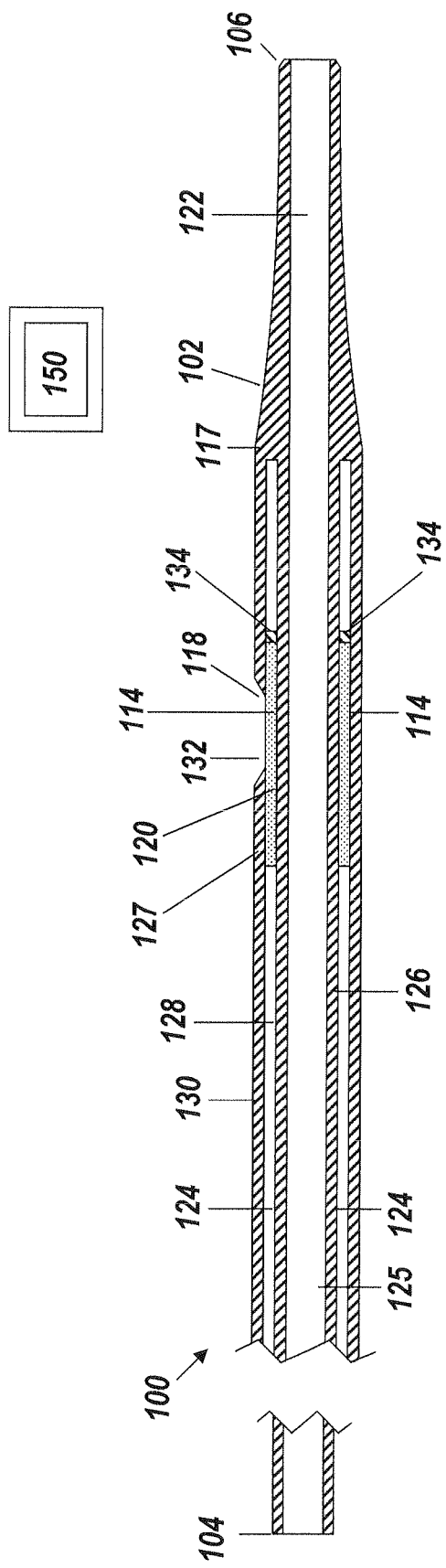
FIG. 7 is a side elevational view in cross-section of a fluid delivery device according to one aspect of the present invention, illustrating a fluid delivery device having a micro-lumen sandwiched between an inner and outer lumen.
Figure 8:
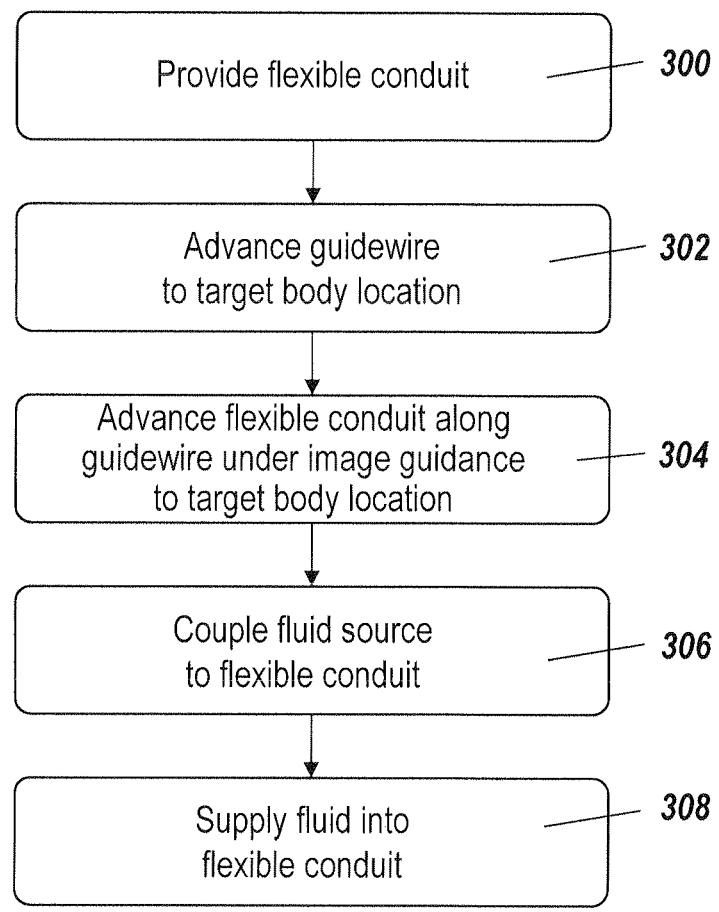
FIG. 8 is a flow chart illustrating the steps of delivering a fluid to a target vessel according to one aspect of the present invention.

In accordance with another example embodiment, FIG. 7 illustrates a monolithic construction of the fluid delivery device 100 in which the micro-lumen 114 of the flexible conduit 102 is sandwiched between an outer surface 126 of an inner lumen 122 and an interior surface 127 of an outer lumen 124. As illustrated in FIG. 7, the flexible conduit 102 has a proximal end 104, a distal end 106, and an inner lumen 122 extending along a longitudinal axis between the proximal end and the distal end. The inner lumen 122 has an interior surface 125 and an outer surface 126 and forms a substantially cylindrical shape. The inner lumen 122 can be adapted to receive a guidewire (not shown) along which the flexible conduit 102 can be advanced under image guidance to a target treatment site within a body lumen, such as the lumen of an artery, for example, for the delivery of fluid. In accordance with some example embodiments, the inner lumen 122 is a guidewire lumen.

The outer lumen 124 of the flexible conduit 102 has a substantially cylindrical shape and is situated circumferentially about the inner lumen 122. As such, the inner lumen 122 occupies a substantial portion of the space within the outer lumen 124. The outer lumen 124 is further defined by an inner wall 128 comprising the outer surface 126 of the inner lumen 122 and an outer wall 130 which provide a fluid flow path extending along at least a portion of an interior of the flexible conduit 102. The coaxial placement of the inner lumen 122 within the outer lumen 124 restricts fluid flowing through the outer lumen thereby causing a non-laminar flow of fluid along the fluid flow path.

The outer wall 130 can be provided with a skive hole 132 which forms an exit 118 through and out the outer wall of the outer lumen 124. In accordance with some example embodiments, a radiopaque marker (not shown in FIG. 7), can be placed adjacent to the skive hole 132 to provide an image guided location adjacent to the skive hole 132. The image guided skive hole 132 provides an image guided exit 118 through and out the outer wall of the outer lumen 124. The outer wall 130 defines a maximum outer diameter of the flexible conduit 102. As described elsewhere herein, the maximum outer diameter of the flexible conduit 102 allows the flexible conduit to track through body lumens having narrow lumen diameters. In accordance with some example embodiments, the maximum outer diameter of the flexible conduit 102 is about 1.1 mm or less. In accordance with some example embodiments, the maximum outer diameter of the flexible conduit 102 is about 0.5 mm, about 0.6 mm, about 0.7 mm, about 0.8 mm, about 0.9 mm, about 1.0 mm or up to about 1.1 mm. In accordance with some example embodiments, the outer wall 130 has a coating 117 as described in detail herein.

As noted above, and as illustrated in FIG. 7, the micro-lumen 114 is sandwiched between the outer surface 126 of the inner lumen 122 and the interior surface 127 of the outer lumen 124, and is positioned adjacent to the skive hole 132. The micro-lumen 114 is in fluid communication with the outer lumen 124 and the skive hole 132 so as to provide fluid communication between the outer lumen and a body lumen within which the flexible conduit 102 is being deployed for delivery of fluid. In accordance with some example embodiments, the micro-lumen 114 redirects fluid flowing in the outer lumen 124 along the longitudinal axis of the flexible conduit 102 from a longitudinal direction to a radial direction toward the exit 118. Redirecting the fluid flowing in the outer lumen 124 in such a manner allows the flexible conduit 102 to direct fluid directly towards a body channel wall. As the fluid is being redirected through the micro-lumen 114, the micro-lumen restricts the fluid flow so that fluid weeps through and out the exit 118 directly towards a body channel wall with atraumatic force so as to avoid trauma to the body channel. The direct delivery of fluid towards a channel wall can be particularly advantageous for treating a condition of the channel, such as an aneurysm, for example. In instances in which the one or more markers (not shown) is positioned adjacent to the skive hole 132, the micro-lumen 114 can be visualized for precise placement of the flexible conduit 102 for such treatment. In accordance with some example embodiments, the micro-lumen 114 has a maximum cross-sectional flow area to restrict the flow of fluid flowing through the exit 118. In accordance with some example embodiments, the maximum cross-sectional flow area of the micro-lumen 114 is 0.01 mm. In accordance with some example embodiments, the micro-lumen 114 comprises a polymer sleeve. In accordance with some example embodiments, the micro-lumen 114 comprises an ePTFE sleeve.

In accordance with some example embodiments, an adhesive 134 is employed at one end of the micro-lumen 114 for sealing the micro-lumen.

Referring now to FIG. 2A. The micro-lumen 114 of the example embodiment illustrated in FIG. 2A shows a micro-lumen 114 having a generally circular cross-sectional shape. Although other cross-sections, such as oval or elliptical, for example, can be utilized, depending on a particular application.

The micro-lumen 114 is generally constructed from a biocompatible material. In accordance with one example embodiment, the biocompatible material is a thermoplastic polymer. Examples of suitable thermoplastic polymers include, but are not limited to polyether block amides (PEBA), polyurethanes, engineering thermoplastics, such as Hytrel (Du Pont), PTFE or FEP, ETFE, or combinations thereof. In certain embodiments, the biocompatible material may include a reinforcement to increase flexibility and kink resistance of the flexible conduit while maintaining a low profile and thin-walled flexible conduit. Examples of suitable reinforcements include braided wire structures or helical coil reinforcements. In such embodiments, the reinforcements can be constructed of stainless steel or nitinol.

FIGS. 2A, 3A, 5A and 6A illustrate exemplary embodiments in which the micro-lumen 114 forms a single exit 118 through and out the distal end 106 of the flexible conduit 102. In accordance with alternative exemplary embodiments, such as those shown in FIGS. 2B, 3B, 5B and 6B, the micro-lumen 114 includes a plurality of micro-lumens 120. The plurality of micro-lumens 120 each can be provided with a maximum cross-sectional flow area aggregating to form a sum of all maximum cross-sectional flow areas. The sum of all maximum cross-sectional flow areas can be customized to suit the needs of a particular application by modifying the cross-sectional flow area of each of the plurality of micro-lumens 120. Controlling the sum of all maximum cross-sectional flow areas permits the fluid flowing through the fluid flow path to exit the plurality of micro-lumens 120 into a target body channel at a sufficiently low pressure (e.g., arterial pressure) such that damage to tissue proximal to the distal end 106 of the flexible conduit 102 within the target vessel to be treated is minimized and/or avoided.

The plurality of micro-lumens 120 as illustrated in FIGS. 2B, 3B, 5B and 6B are distributed in a substantially uniform manner and have a substantially uniform diameter, However, in alternative embodiments, the plurality of micro-lumens 120 can be distributed in a non-uniform manner and have varying diameters (not shown).

In accordance with another example embodiment, FIG. 9 and FIGS. 10A, 10B, and 10C illustrate the flexible conduit 102 provided with a lumen extending along an interior of the flexible conduit and a port 135 (e.g., a fluid infusion port) that allows for fluid delivery to a targeted treatment site within a body lumen at a pressure sufficient to minimize or avoid damage to the body lumen (e.g., without jetting). The lumen provides a fluid flow path between the proximal end and the distal end for a fluid injected into the conduit. The lumen transitions into a micro-lumen exiting from the flexible conduit at the port at the image viewable zone 144. The fluid infusion port 135 achieves such fluid delivery through its shape which comprises an elongated half-funnel with side wall baffles 139 (shown in FIGS. 10A, 10B and 10C). The shape of the fluid infusion port 135 provides a fluid flow path defined by a restricted cross-sectional area, which restricts the flow of fluid so that fluid exiting the fluid infusion port exits without jetting regardless of the input pressure at which the fluid enters the fluid flow path. The shape of the fluid infusion port 135 also provides for a low fluid exit angle, which is parallel to the central longitudinal axis of the flexible conduit 102, causing the fluid to exit primarily laterally along the length of the conduit 102, rather than perpendicular to, or outward from, the conduit 102. In addition to preventing jetting of fluid, the low fluid exit angle of the fluid infusion port 135 permits the flexible conduit 102 to deliver fluid to a target body lumen in a way that fills the space between the body lumen and the flexible conduit proximate to one or more markers 119 viewable in vivo by an imaging device 150 disposed along an exterior of the flexible conduit at a predetermined location suitable for delivery of a fluid from the device. Said differently, the fluid infusion port 135 delivers fluid, under image guidance using one or more radiopaque markers 119 forming an image viewable zone 144, to a narrow body channel without jetting fluid into the walls of the narrow body channel, so as to avoid or minimize damage to the narrow body channel. In certain embodiments, the flexible conduit 102 can be provided with multiple ports 135 (not shown) along the length of the flexible conduit. In such embodiments, each of the fluid infusion ports 135 may be provided with a fluid micro-lumen. In such embodiments, each of the fluid infusion ports 135 may use the same fluid micro-lumen. In such embodiments, some fluid infusion ports 135 may be provided with a distinct fluid micro-lumen while some fluid infusion ports may share the same fluid micro-lumen.

In accordance with some example embodiments, the one or more markers 119 (e.g., radiopaque markers) form an image viewable zone 144 that allows a user of the present fluid delivery device 100 to determine in real-time the highest possible concentration of fluid, such as a medication, therapeutic agent, or diagnostic, that can be delivered under image guidance utilizing an imaging device 150 out and through the infusion port 135 along the image viewable zone 144 on the outside of the flexible conduit 102. Although there are three radiopaque markers 119 shown in the example embodiment shown in FIGS. 9, 10A and 10B, it should be appreciated that any number of radiopaque markers 119 (e.g., 1, 2, 3, 4, or up to 5 or more) can be used to form the image viewable zone 144, depending on the particular application. The image viewable zone 144 allows a user of the device 100 to precisely position the flexible conduit 102 adjacent to a targeted body site to be treated so that a maximum concentration of a fluid medication can be delivered to the target site. The combination of a maximum outer diameter D (e.g., D1 and D2) and the image viewable zone 144 permits the present fluid delivery device 100 to access more difficult to reach and remote target treatment sites for the highest possible concentration delivery of a fluid medication to the difficult to reach site. For example, the maximum outer diameter D permits the flexible conduit 102 to access body cavities, channels or lumens in areas adjacent to capillary channels to deliver sufficiently high concentrations of a fluid medication locally to impart a therapeutic effect. In some embodiments, the maximum outer diameter D of the flexible conduit 102 permits the fluid delivery device 100 to access minute capillary channels, such as capillary channels that are used to deliver nutrients driving tumor growth, for example. In this regard, the present fluid delivery device 100 can be used for oncology applications to perform image guidance chemotherapy for the localized delivery of the highest concentration of a chemotherapeutic agent to a vessel adjacent to a capillary channel such that the chemotherapeutic agent imparts a therapeutic effect on the tumor without causing undesirable systemic effects. In some example embodiments, the flexible conduit 102 is provided with a first maximum outer diameter D1 and a second maximum outer diameter D2 that is proximate to the image viewable zone 144. The second maximum outer diameter D2 proximate to the image viewable zone 144 allows the flexible conduit to penetrate more distal and difficult to reach, spatially restricted treatment sites within the body that are closer to an intended targeted organ, tissue space, cavity, etc. for delivery of an optimal amount of therapeutic agent to the targeted organ, tissue space, cavity, etc. In accordance with some example embodiments, the highest possible concentration of a drug can be delivered under direct image guidance using an imaging device 150 to view the image viewable zone 144.

As shown in FIG. 9, the flexible conduit 102 can be provided with a rapid exchange port 133 for rapid exchange of the flexible conduit during use.

Figure 10A:
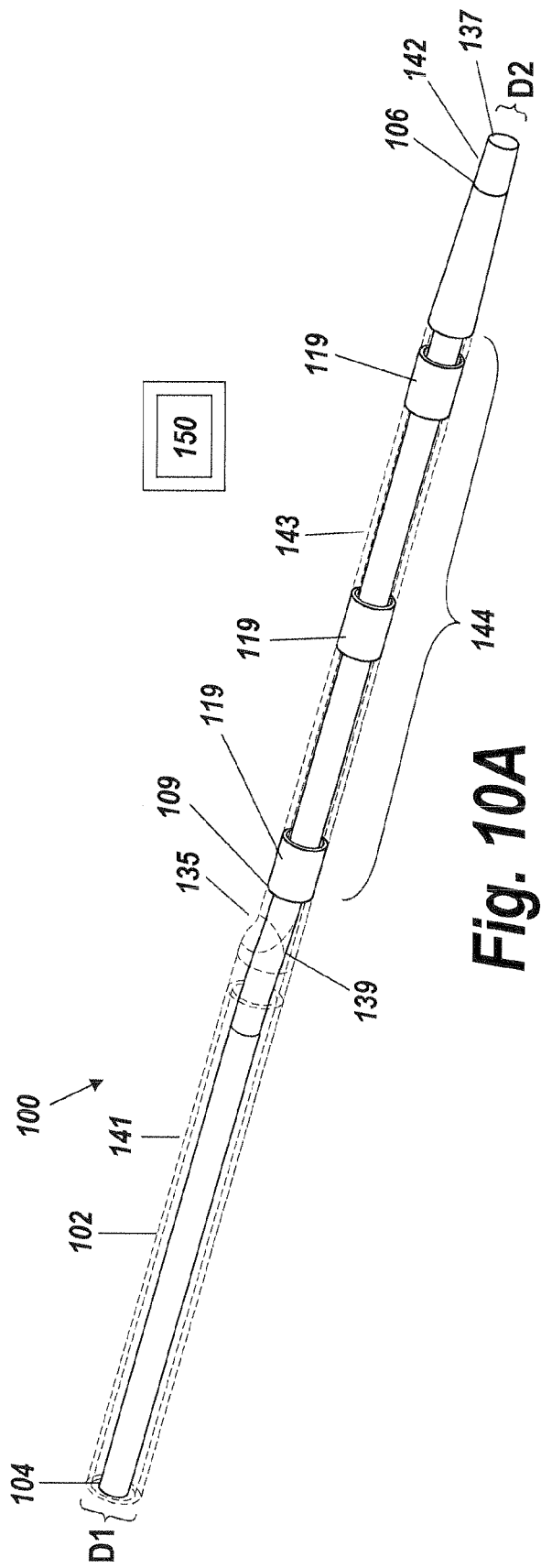
FIG. 10A is a perspective view of the fluid delivery device shown in FIG. 9 according to one aspect of the present invention, illustrating the port and markers forming an image viewable zone for delivering fluid to a target body lumen under image guidance utilizing an imaging device.
Figure 10C:
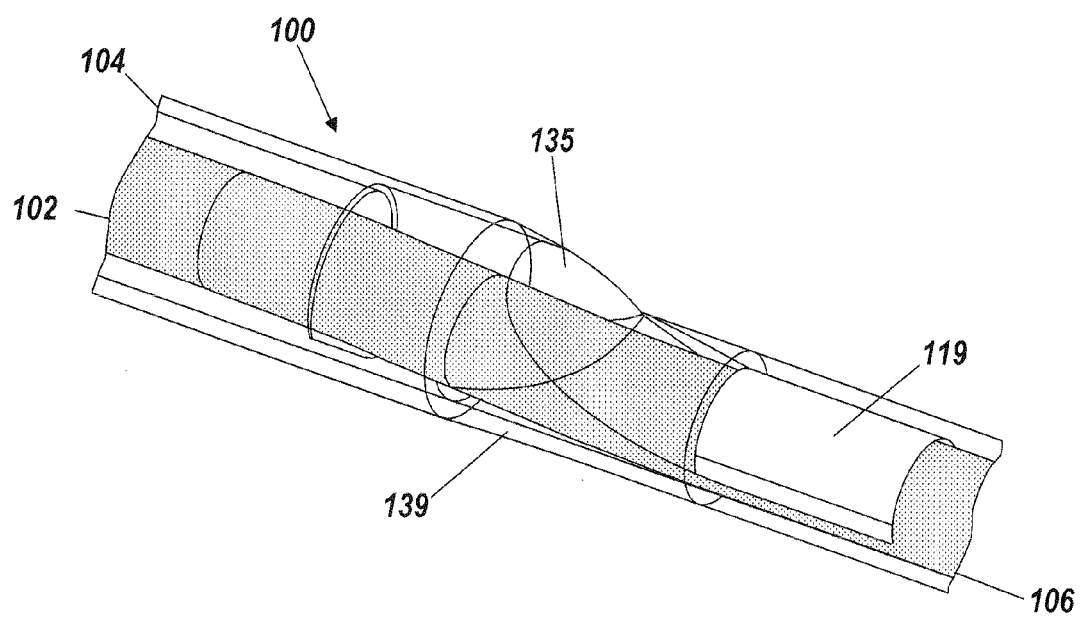
FIG. 10C is an exploded perspective view of the port illustrated in FIG. 10B, according to one aspect of the present invention.

In certain embodiments, such as the example embodiment shown in FIGS. 9, 10A and 10B, the flexible conduit 102 can also be provided with a guidewire exit, which facilitates advancement of the flexible conduit 102 along a guidewire (not shown).

As noted above, the flexible conduit 102 can also be provided with one or more markers 119 (e.g., radiopaque markers) to form an image viewable zone 144 to permit the flexible conduit 102 to deliver fluid to a target narrow body channel under image guidance. The radiopaque markers 119 for image guidance can be incorporated into the flexible conduit 102 in a number of ways. For example, image guidance can be imparted to the flexible conduit 102 by using radiopaque markers 119 composed of heavy radiopaque metals, including, but not limited to PtIr, Au, tungsten, or other similar heavy radiopaque metals. In some embodiments, image guidance can be imparted to the flexible conduit 102 by using radiopaque paints or coatings (e.g., dispersions). In some embodiments, image guidance can be provided by a coating applied, painted, etched, grafted, printed, or laminated on one or more locations of the flexible conduit. In other embodiments, image guidance can be imparted to the flexible conduit 102 by incorporating radiopaque fillers, such as barium sulfate, tungsten or bismuth subcarbonate, for example, into the polymer materials used to construct the flexible conduit. It should be noted that the spacing, size, and placement of the radiopaque markers 119 for image guidance may vary along the longitudinal length of the flexible conduit 102. It should be appreciated by those skilled in the art that the image viewable zone 144 can be used for image guided fluid delivery utilizing any suitable imaging device 150 now known or later developed. Suitable imaging devices 150 include those imaging devices utilizing image viewing technology such as radiography, magnetic resonance imaging, nuclear imaging, photo acoustic imaging, thermal imaging, and ultrasound, to name but a few examples.

The relative distances between the rapid exchange port 133, the infusion port 135, the radiopaque markers 119, and the guidewire exit 137 provide the fluid delivery device 100 of the present invention with a variable image guidance means that can be used to optimize fluid delivery to a target spatially restrictive, tortuous body lumen for treatment. In accordance with one example embodiment, the distance between the rapid exchange port 133 and the infusion port 135 can be between about 1 cm and about 40 cm. In accordance with one example embodiment, the distance between the infusion port 135 and the guidewire exit 137 can be between about 5 mm and about 50 mm. For example, the distance between the infusion port 135 and guidewire exit 137 can be between about 5 mm, about 6 mm, about 7 mm, about 8 mm, about 9 mm, about 10 mm, about 10-15 mm, about 16-20 mm, about 20-30 mm, about 31-40 mm, or about 41, about 42, about 43, about 44, about 45, about 46, about 47, about 48, about 49, or up to about 50 mm.

Still referring to FIGS. 9 and 10A, 10B and 10C, the flexible conduit 102 can be provided with a transition in outer diameter along the longitudinal length of the flexible conduit 102. The transition in outer diameter provides stiffness transitions between a first region 141 spanning from the proximal end 104 to proximate to the medial portion 109 and a second region 143 spanning from proximate to the medial portion 109 to the distal end 106 of the flexible conduit 102. The stiffness transitions provide improved flexibility and torque response of the flexible conduit 102 at the distal end 106, as well as improved trackability and navigation in vivo through narrow, spatially restricted, tortuous body channels. In accordance with one example embodiment, the second region 143 can be provided with a maximum outer diameter smaller than the outer diameter of the first region 141. For example, the maximum outer diameter of the second region can be between 0.0270 inches and 0.0360 inches. In some embodiments, the flexible conduit 102 is provided with a terminal portion 142 which has a maximum outer diameter smaller than the first region 141 and the second region 143. In certain embodiments, the terminal portion 142 has a maximum outer diameter of 0.0240 inches. In certain embodiments, the terminal portion 142 has a tapered configuration. In accordance with another example embodiment, the second region 143 of the flexible conduit 102 is provided with multiple sections of polymers having varying durometers (e.g., softness) to permit flexibility transitions between sections thus improving the flexibility, torque response and deliverability of the flexible conduit 102 in vivo into narrow, spatially restricted, and tortuous body channels, as well as channels of delicate tissue such that the terminal portion 142 is provided with a maximum softness as compared to other regions of the flexible conduit 102. Providing the terminal portion 142 with a maximum softness in this manner renders the terminal portion highly atraumatic to the tissue, thereby aiding the flexible conduit 102 in vivo in navigating the spatially restricted, tortuous, and delicate narrow body channel. It should be appreciated that such flexibility transitions may be gradual or abrupt along the longitudinal length of the flexible conduit 102 from the proximal end 104 to the distal end 106 and terminal portion 142, depending on the desired performance, as understood by those skilled in the art. In certain embodiments, the distal end 106 and terminal portion 142 may be comprised of a material having a high durometer such that the second region 143 of the flexible conduit 102 exhibits improved stiffness and pushability for entering and navigating narrow, stenosed body channels or channels in vivo comprised of hard, calcified materials such as in a calcified lesion in an artery. In some embodiments, the flexible conduit can be constructed of materials having varying durometers to improve flexibility and torque response during navigation in vivo within narrow or tortuous body lumens or cavities. The durometers may range from about 50 to 100 shore A and 40 to 80 shore D.

The fluid delivery device 100 of the present invention can be used as a medical treatment device for treating a body channel, (e.g., a vessel, such as a native vessel, a stented vessel, or a surgically repaired and or synthetic repaired vessel or graft, for example). The medical treatment device can be used to treat a wide range of body channels characterized by a narrow channel diameter (e.g., less than one millimeter) including channels of the distal coronary vasculature, peripheral vasculature, gastrointestinal tract, urological cavities and lumens, the luminal lymphatic system common to cancer cell deposition and the delicate and tortuous vessels comprising the neurovasculature, for example. In accordance with an example embodiment, the body channel is a cardiovasculature vessel. In accordance with an example embodiment, the body channel is the lymphatic system. In accordance with an example embodiment, the body channel is an organ cavity with latched capillary channels which connect to a tumor. In accordance with an example embodiment, the body channel is a pulmonary vessel. In accordance with some example embodiments, the fluid delivery device can be used as a medical diagnostic device for diagnosing a disease in a body lumen, organ cavity and surgically created body following surgical intervention.

The fluid delivery device 100 of the present invention can be used for a variety of medical treatments including, but not limited to: preceding or immediately following dilation of stenoic blood vessels in a percutaneous transluminal angioplasty procedure (PICA or PTA), preceding or immediately following removal of thrombi and emboli from obstructed blood vessels, preceding or immediately following urethra dilation, to treat prostatic enlargement due to benign prostate hyperplasia (BPH) or prostatic cancer, to treat malignant or benign tumors adjacent to or nearby capillary channels, to selectively treat a hard to reach tissue infection, to provide direct visual drug delivery guidance during therapeutically treating occlusive stroke conditions, for treating aneurysms medically, or for restoring patency from occlusion to body passages such as blood vessels, the urinary tract, the intestinal tract, the kidney ducts, or other body passages and cavities which under image guidance a high concentration of a medication can effectively improve the targeted occlusion location to restore biological fluid flow.

In accordance with some example embodiments, the fluid delivery device 100 can be used to treat cancerous tissue e.g., tumors. In such instances, the maximum outer diameter of the flexible conduit 102 adjacent to the image viewable zone 144 allows the fluid delivery device 100 to access vessels adjacent to capillary channels that supply tumors to permit a user of the device to visualize the delivery of a fluid medication (e.g., chemotherapeutic agent) so that the user can determine in real-time the highest effective concentration to be delivered to impart a therapeutic effect. For oncology applications, the present fluid delivery device 100 allows delivery of high concentrations locally to a target tumor without resulting in systemic unwanted effects associated with conventional chemotherapy by delivery fluid directly into the minute vessels adjacent to the capillary channels that directly supply the tumor with blood cell carrying nutrients necessary for tumor survival. For example, the present fluid delivery device 100 can be used to optimize the most effective drug concentration to a localized region of the body, such as brain, breast, pancreas, lymph node, for example, by allowing the user to visualize delivery of the medicated fluid out through the infusion port 135 primarily laterally along the image viewable zone 144 of the outside of the flexible conduit 102. In this regard, the image viewable zone 144 allows the user to precisely position the flexible conduit 102 within the vessel adjacent to the capillary channel such that that a maximum amount of fluid will be delivered to the target location to achieve a chemotherapeutic effect on the tumor without causing significant damage to healthy tissue and cells.

A variety of therapeutic agents can be delivered with the fluid delivery device 100 of the present invention. The localized delivery of thrombolytics, such as heparin, tissue plasminogen activating compounds such as TPA or anti-platelet medications which have been reported to take on powerful lytic affects when delivered in high concentrations locally within a vessel, or when directly to the surface of occluded or thrombosed vascular grafts as in the superficial femoral artery, or used as a dialysis access graft or native body vessels where such concentrations of medication can inhibit the clotting of the graphs, capillary channels or native body vessels or body cavities such as the urethra. The fluid delivery device 100 of the present invention thus can be used as a balloonless medication thrombolectomy catheter to remove facilitate biochemical degradation of biomass formations and obstructions from body organs, body cavities, surgically installed vascular conduits or native body vessels while concomitantly delivering thrombolytics along the targeted image guided location will enable a desired clinical effect without significant systemic dosing, systemic dilution or remote tissue side effects. In the instance of the fluid medication flowing through the fluid flow path of the flexible conduit 102, the fluid can exit through the micro-lumens in an accumulating low pressure weeping manner to a target location in the patient body viewable under image guidance. The fluid medication, in such an instance, can have therapeutic characteristics and contain one or more agents having therapeutic properties for measurable clinical benefit of the affected target location during and or immediately following fluid medication delivery under image guidance. Example agents can include those listed in Table 1 below. In some embodiments, the fluid medication injected through the fluid flow path is an emulsion with one or more therapeutic agents. In some embodiments, the emulsion is a nanoemulsion consisting of one or more nanoparticle therapeutic agents. In some embodiments, the therapeutic fluid injected through the fluid flow path is a cellular suspension comprised of cellular, genetic or viral materials.

In accordance with an example embodiment, for instance, the fluid delivery device 100 of the present invention can be used to deliver a gene therapy therapeutic agent to a targeted, hard to reach and remote body location for capillary distribution of a gene therapy medium (e.g., flexible conduit mediated delivery of a vector). As used herein "gene therapy" refers to the insertion, alteration, or removal of genes, genetic material (e.g., nucleic acids), or the insertion, alteration, or removal of an expression product (e.g., protein) of those genes, at the cellular level, whether in vivo or in vitro, to treat or prevent a disease, or to alleviate the symptoms or minimize reoccurrence of the symptoms associated with a disease. In such instances, the fluid delivery device 100 can be used to locally deliver the highest concentration of a gene therapy therapeutic agent to a targeted narrow diameter vessel or capillary channel. The fluid delivery device 100 of the present invention can be used to infuse mediums (e.g., solutions, dispersion, emulsion, etc.) containing one or more gene therapy vectors directly into a target tissue or body lumen (e.g., vessel or capillary), for instance, for the local delivery of such gene therapy vectors to remote portions of the endothelium, tunica media, and/or adventitial layer of a patient's vasculature. The fluid delivery device 100 can also be used for the infusion of a gene therapy vector directly into a target organ tissue (e.g., intracoronary) or for the direct transfer of genes into the wall of a targeted vessel (e.g., intestine, kidney, brain). Such localized delivery can be used, for example, to improve and/or facilitate localized tissue repair subsequent to mechanical injury or mechanical reperfusion events (e.g., thrombus extraction, thrombolysis, angioplasty, thrombectomy, and stenting, etc.). It should be appreciated that any suitable vector now known or later developed can be used to package a gene therapy vector containing one or more transgenes into a medium for gene delivery with the fluid delivery device 100. Examples of suitable vectors include, for instance, adenovirus vectors, adeno-associated virus vectors, synthetic oligonucleotides, and synthetic vectors (e.g., liposomes, for example cationic liposomes, polymers, dendrimers, cell-penetrating peptides, etc.). In an example embodiment, pre-flushing the fluid delivery device 100 with a serum albumin solution can be performed prior to vector administration to minimize the risk of viral vector inactivation. In certain embodiments, delivery of a gene therapy product or multiple gene therapy products to a targeted vessel or capillary can promote the regeneration of the vessel or capillary. For example, the fluid delivery device 100 of the present invention can be used to deliver a combination of growth factors (e.g., vascular endothelial growth factor (VEGF), fibroblast growth factor (FGF), platelet derived growth factor (PDGF), and basic fibroblast growth factor (BFGF), and various isoforms thereof) to a targeted tissue for repair or regeneration of the tissue. The fluid delivery device 100 of the present invention can also be used to effectively deliver high concentrations of a single growth factor to a targeted narrow diameter vessel or minute capillary channel. Examples of growth factors that can be used, either alone, or in any combination, to improve vascular tissue repair include FGF9, VEGF 121, VEGF 165, VEGF 189, VEGF 206, PDGF-BB, and BFGF.

Delivering high concentrations of gene therapy products (e.g., growth factors) under direct image guidance with the fluid delivery device 100 of the present invention to improve vascular tissue repair may be advantageous in the treatment of chronic vascular diseases that involve chronic vascular occlusions, such as peripheral vascular disease (PVD), coronary artery disease (CAD), Pulmonary Embolism (PE) treatment, Deep Vein Thrombosis (DVT), or regeneration of damaged glandular organ, tubular organ tissue or muscle tissue. In accordance with some example embodiments, the application of gene therapy using the fluid delivery device 100 of the present invention can be performed in combination with ultrasound to increase the probability of successful delivery of the gene therapy product. For example, a combination of vascular growth factors can be delivered using the fluid delivery device 100 of the present invention while at the same time performing an echocardiography to help alleviate symptoms associated with chronic vascular disease (e.g., chronically compromised blood flow) to improve blood flow following tissue repair. By way of illustration and not of limitation, for example, carrier microbubbles (e.g., cationic lipid microbubbles which are charge-coupled to plasmid DNA containing a vector having desired genetic material) can be used with an ultrasound to improve gene delivery to the target vessel or capillary.

The fluid delivery device 100 of the present invention can be used to administer gene therapy using multiple gene (e.g., one or more) therapy products over multiple different time points to increase vascular repair and restore or enhance blood flow. Gene delivery at multiple time points may be advantageous because different growth factors act at different and specific stages of vascular growth. For example, growth factor VEGF has been shown to be effective at initiating angiogenesis, however VEGF alone may not be enough to form the complex vascular networks needed for improved vascular repair and restored blood flow. In addition, other growth factors perform distinct functions, such as PDGF which stimulates blood vessel maturation by recruiting smooth muscle cells to endothelium of emerging vessels. As such, in accordance with an example embodiment, the fluid delivery device 100 of the present invention can be used to deliver multiple gene therapy products (e.g., growth factors) at multiple different time points to enhance the success of gene therapy as well as to ensure that the right gene therapy products are delivered at the right time. For example, a first gene therapy product (e.g., gene therapy vector) or combination of gene therapy products can be delivered at a first time point, followed by delivery of a second gene therapy product or combination of gene therapy products, and a third delivery of a third gene therapy product or combination of gene therapy products, followed by up to an $n^{th}$ delivery of an $n^{th}$ gene therapy product or combination of gene therapy products, where n is an integer. It should be appreciated that at each different time point a different gene therapy product or combination of gene therapy products can be delivered, depending on the particular application, as understood by those of skill in the art. If multiple genes are to be delivered at a single time point, it should also be appreciated that these genes can be delivered via multiple vectors each having a gene incorporated into the vector, or delivered via one or more vectors each having multiple genes incorporated therein.

TABLE #1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates, cyclosporine |
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab, eptifibatide, Ticagrelor |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate, Tenectaplase, Microplasmin, Plasmin, Desmoteplase, Alfimeprase |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes, thrombin |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibitation of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, |

TABLE #1-continued

| CLASS | EXAMPLES |
|---|---|
| | mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma-1b, Interluekin-10 |
| Immunosuppressive/Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase, 3-bromopyruvate, melphalan |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase, siRNA |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |
| Vasodilators | Niroglycerin, sodium nitroprusside, calcium channel blockers (nicardipine, verapamil) |
| Neuroprotective/Neuronal healing agents | N-methyl-D-aspartate receptor antagonists, Nalmefene, Lubeluzole, Clomethiazole, calcium channel blockers, tirilazad, NXY-059, monoclonal antibodies (Enlimomab, Hu23F2G), Tetracycline antibiotics (minocycline), Citicoline, fibroblast growth factors (Fiblast) |

The inclusion of a drug or agent in the fluid flowing through the micro-lumens as made possible by the method of manufacture of the present invention eliminates, or substantially reduces, systemic responses linked with conventional oral or intravenous therapies. The reduction of drug permeability effects through tissues is due to the ability to target application of the drug or agent to specific locales. The ability to incorporate the drug or agent in the fluid flowing through the flexible conduit 102 makes it possible to load the fluid delivery device 100 with concentrations substantially greater than existing device coating technologies. Further, the release of the drug or agent can be continuous over longer periods of time leading to longer residence times.

One example use for the fluid delivery device 100 is in the application of a contrast agent, or dye, with and without therapeutic agents mixed as part of the deliverable fluid medication for enabling enhanced image zone visualization of the high concentration of fluid medication within a patient. The fluid delivery device 100 of the present invention provides a minimal pressure flow environment with an image viewable high concentration medication zone within a body lumen that minimizes systemic dilution around the device image viewable medication zone with minimal distal medication washout. The device further provides a minimal pressure perfusion or permeation of the contrast agent or dye to permit visualization of vessels or other target locations within the body, with or without fluid medication. The minimal occlusion together with minimal pressure flow reduces damage to tissue proximal to the device by dissection or wall jetting that otherwise might occur using higher pressure devices. By controlling the size, profile, exit hole location in relation to the area of high concentration of medication zone along the image viewable zone and having the ability to vary the volume of fluid medication capacity and location characteristics of the micro-lumen exit sites and pressure requirements for attaining the highest level of medication or radiopacity potential or a radiopaque fluid along the image viewable zone can be further modified for various anatomical body cavity orientation within the target locations, as understood by one of skill in the art.

The fluid delivery device 100 can be used for the delivery of large volumes of fluid over extended durations (e.g., about 100 ml over about 2 hours), having high concentrations of a medication, to a target body lumen 101 in an atraumatic manner such that damage to tissue proximal to the distal end 106 of the flexible conduit 102 within the target body lumen is avoided or minimized. Delivering the therapeutic fluid medication to the target tissue location in the body lumen 101 can be accomplished by first advancing a guidewire (step 302) to a target tissue location within the body lumen to be treated with the therapeutic fluid medication. Next, a flexible conduit 102 of the present invention is advanced (step 304) under image guidance along the guidewire until the distal end 106 of the flexible conduit 102 reaches a lumen within the target body channel 101. A fluid source can be coupled (step 306) to the proximal end 104 of the flexible conduit 102 to supply the therapeutic fluid (step 308) into the flexible conduit so that the therapeutic fluid exits through and out the port primarily laterally along the image guided location 115, or image viewable zone 144, at the distal end 106 of the flexible conduit through the micro-lumens at a rate and a pressure insufficient to damage tissue within the target body channel 101 proximal to the distal end of the flexible conduit.

The fluid delivery device 100 of the present invention provides a number of advantages over existing fluid delivery devices. For example, the flexible conduit 102 is capable accessing difficult to reach sites, such as those which can be reached by navigating tortuous, spatially restricted body anatomy. The fluid delivery device 100 is also capable of accessing body channels defined by narrow channel diameters, e.g., as narrow as about 1 millimeter in diameter, for the maintaining a high concentration of fluid medication at a target treatment site within the body channel at an image guided location. In this regard, the fluid delivery device 100 is not restricted in the same manner as existing fluid delivery devices which employ an inflatable mechanism, such as a balloon catheter, for example. As such, the fluid delivery device 100 of the present invention can be used to treat channels of the neurovasculature and conditions relating to impaired channels therein. The fluid delivery device 100 of the present invention is capable of delivering a therapeutic fluid medication to a target location in the patient's body without using an expansion force that could otherwise damage tissue proximal to the distal end 106 of the fluid delivery device 100.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A fluid delivery device, comprising:
   a flexible conduit having a proximal end and a distal end;
   an image viewable zone disposed along an exterior of the flexible conduit at a predetermined location suitable for delivery of a fluid from the device and proximally located with respect to the distal end, the image viewable zone defined by one or more markers viewable in vivo by an imaging device; and
   a lumen extending along an interior of the flexible conduit providing a fluid flow path between the proximal end and the distal end for a fluid injected into the flexible conduit, the lumen transitioning from a portion having a first cross-sectional flow area into a micro-lumen having a second cross-sectional flow area less than the first cross-sectional flow area, the micro-lumen exiting from the flexible conduit at a port at the image viewable zone, the port configured in such a way as to direct fluid out through the port along a longitudinal length of the flexible conduit and the image viewable zone in a direction primarily parallel with respect to a longitudinal axis of the flexible conduit, the port having a first cross-sectional flow area that is less than a second cross-sectional flow area.

2. The fluid delivery device of claim 1, wherein the device is constructed of one or more biocompatible materials.

3. The fluid delivery device of claim 2, wherein the one or more biocompatible materials comprise a thermoplastic polymer.

4. The fluid delivery device of claim 3, wherein the thermoplastic polymer is selected from the group consisting of PEBA, nylon HDPE, PTFE, FEP, ETFE, ePTFE and combinations thereof.

5. The fluid delivery device of claim 1, further comprising a reinforcement incorporated into the flexible conduit imparting flexibility and kink resistance to the flexible conduit.

6. The fluid delivery device of claim 5, wherein the reinforcement comprises a braided wire structure, slotted metal tube, or a helical coil structure.

7. The fluid delivery device of claim 5, wherein the reinforcement is constructed of a material selected from the group consisting of stainless steel, cobalt, chromium, platinum, nitinol, and combinations thereof.

8. The fluid delivery device of claim 1, wherein the flexible conduit has an outer diameter that varies along the image viewable zone imparting improved flexibility and torque response to the flexible conduit during navigation in vivo.

9. The fluid delivery device of claim 1, wherein the flexible conduit is comprised of multiple sections, each section constructed of materials of varying durometer, imparting improved flexibility and torque response during navigation in vivo.

10. The fluid delivery device of claim 1, wherein the flexible conduit comprises varying durometer ranges along its length ranging from about 50 to about 100 shore A and from about 40 to about 80 shore D.

11. The fluid delivery device of claim 1, wherein the one or more markers comprise heavy radiopaque metal component materials.

12. The fluid delivery device of claim 11, wherein the heavy radiopaque metal component materials are selected from the group consisting of PrIr, Au, tungsten, and combinations thereof.

13. The fluid delivery device of claim 11, wherein the one or more markers comprise radiopaque fillers incorporated into one or more locations along the flexible conduit.

14. The fluid delivery device of claim 13, wherein the radiopaque fillers are selected from the group consisting of barium sulfate, tungsten, and bismuth subcarbonate.

15. The fluid delivery device of claim 1, wherein the one or more markers are comprised of a coating applied, painted, printed, etched, grafted, or laminated onto the flexible conduit forming the image viewable zone.

16. The fluid delivery device of claim 1, wherein fluid flowing through the fluid flow path exits the port into a target body location at a rate insufficient to damage tissue.

17. The fluid delivery device of claim 1, wherein if a fluid having a viscosity of 1 cps at 25° C. is supplied to the flexible conduit at a pressure of between about 1 atmosphere and about 4 atmospheres, a flowrate through the flexible conduit does not exceed 17 cc/min.

18. The fluid delivery device of claim 1, wherein if a fluid having a viscosity of 5 cps at 25° C. is supplied to the flexible conduit at a pressure of between about 1 atmosphere and about 4 atmospheres, a flowrate through the flexible conduit does not exceed 4 cc/min.

19. The fluid delivery device of claim 1, wherein if a fluid having a viscosity of 11 cps at 25° C. is supplied to the flexible conduit at a pressure of between about 1 atmosphere and about 4 atmospheres, a flowrate through the flexible conduit does not exceed 2 cc/min.

20. The fluid delivery device of claim 1, further comprising a rapid exchange port proximal to the port at the image viewable zone, wherein the relative distances between the rapid exchange port, the port at the image viewable zone, and the one or more markers, provide an image guidance means through which navigation of the flexible conduit through tortuous, spatially restricted body channels can be optimized.

21. The fluid delivery device of claim 1, wherein the flexible conduit has a hydrophilic exterior surface.

22. The fluid delivery device of claim 1, wherein the flexible conduit has a hydrophobic exterior surface.

23. The fluid delivery device of claim 1, further comprising a coating disposed on an exterior surface of the flexible conduit.

24. The fluid delivery device of claim 23, wherein the coating is a lubricious coating.

25. The fluid delivery device of claim 23, wherein the coating is a therapeutic coating.

26. The fluid delivery device of claim 25, wherein the therapeutic coating comprises omega-3 fatty acids.

27. The fluid delivery device of claim 1, wherein the fluid comprises a medication, a therapeutic agent, a diagnostic agent, or any combination thereof.

28. The fluid delivery device of claim 1, wherein the fluid comprises an emulsion, a nanoemulsion, or a cellular suspension comprised of cellular, genetic or viral material.

29. The fluid delivery device of claim 1, wherein the fluid comprises at least one of antioxidants, anti-hypertensive agents, anti-inflammatory agents, anti-infective agents, antibiotic agents, growth factor antagonists, anti-platelet agents, anti-coagulant agents, thrombolytic agents, drugs to alter lipid metabolism, ACE inhibitors, anti-proliferatives, anti-neoplastics, tissue growth stimulants, gasses, agents for promotion of hollow organ occlusion or thrombosis, agents for functional protein or factor delivery, agents for second messenger targeting, angiogenic agents, anti-angiogenic agents, agents for gene delivery, agents for local tissue perfusion, nitric oxide donating derivatives, thrombus-inducing agents, vasodilators, neuroprotective agents, neuronal healing agents, saline, and contrast media.

30. The fluid delivery device of claim 1, wherein the fluid comprises abciximab.

31. The fluid delivery device of claim 1, wherein the fluid comprises eptifibatide.

32. The fluid delivery device of claim 1, wherein the fluid comprises TPA.

33. The fluid delivery device of claim 1, wherein the fluid comprises at least one of a contrast agent or a dye.

34. The fluid delivery device of claim 1, wherein the fluid delivery device is a medical treatment device for treating a body lumen or cavity.

35. The fluid delivery device of claim 1, wherein the fluid delivery device is a medical diagnostic device for diagnosing a disease in a body lumen or cavity.

36. The fluid delivery device of claim 1, wherein the imaging device utilizes image viewing technology in the form of one or more of radiography, magnetic resonance imaging, nuclear imaging, photo acoustic imaging, thermal imaging, or ultrasound.

37. The fluid delivery device of claim 1, wherein the image viewable zone permits a user of the fluid delivery device to observe a region in which the fluid is being delivered in real-time such that the user can determine a concentration of fluid to deliver to a target treatment site within a target body location.

38. The fluid delivery device of claim 1, wherein the port is formed shaped as an elongated half-funnel with side wall baffles facing in the direction primarily parallel with respect to the longitudinal axis of the flexible conduit.

39. The fluid delivery device of claim 1, wherein the direction is oriented distally.

* * * * *